US009856535B2

(12) United States Patent
Handique et al.

(10) Patent No.: US 9,856,535 B2
(45) Date of Patent: Jan. 2, 2018

(54) SYSTEM FOR ISOLATING CELLS

(71) Applicant: DeNovo Sciences, Plymouth, MI (US)

(72) Inventors: Kalyan Handique, Ann Arbor, MI (US); Priyadarshini Gogoi, Ann Arbor, MI (US); Yi Zhou, Plymouth, MI (US); Saedeh Sepehri, Ypsilanti, MI (US); Christopher Siemer, Ypsilanti, MI (US)

(73) Assignee: DeNovo Sciences, Inc., Plymouth, MI (US)

( * ) Notice: Subject to any disclaimer, the term of this patent is extended or adjusted under 35 U.S.C. 154(b) by 0 days.

(21) Appl. No.: 14/289,155

(22) Filed: May 28, 2014

(65) Prior Publication Data

US 2014/0357511 A1 Dec. 4, 2014

Related U.S. Application Data

(60) Provisional application No. 61/829,537, filed on May 31, 2013.

(51) Int. Cl.
*C12Q 1/68* (2006.01)
*G01N 33/574* (2006.01)
(Continued)

(52) U.S. Cl.
CPC ...... *C12Q 1/6886* (2013.01); *B01L 3/502761* (2013.01); *C12Q 1/6834* (2013.01); *C12Q 1/6841* (2013.01); *G01N 33/57415* (2013.01); *G01N 33/57423* (2013.01); *B01L 2200/0668* (2013.01); *B01L 2200/16* (2013.01); *B01L 2300/087* (2013.01);
(Continued)

(58) Field of Classification Search
CPC .......................... C12C 1/6886; B01L 3/502761
USPC .............................................................. 506/9
See application file for complete search history.

(56) References Cited

U.S. PATENT DOCUMENTS 644,134 A 2/1900 Gastineau
4,551,435 A 11/1985 Liberti et al.
(Continued)

FOREIGN PATENT DOCUMENTS

WO 03035909 A2 5/2003
WO 2006098696 A1 9/2006

OTHER PUBLICATIONS

Sugio et al.(Sensors and Acutators, B99, 2004, pp. 156-162).*
(Continued)

*Primary Examiner* — Karla Dines
(74) *Attorney, Agent, or Firm* — Jeffrey Schox; Ivan Wong

(57) ABSTRACT

A system and method for isolating cells, comprising: a substrate having a broad surface; an array comprising a set of wells defined at the broad surface of the substrate, each well including: a base surface, an open surface directly opposing the base surface, defined at the broad surface of the substrate, and configured to receive one of a single cell and a single cluster of cells from a direction perpendicular to the broad surface of the substrate, and a set of channels that fluidly couple each well to at least one adjacent well; wherein the set of wells includes an interior subset and an exterior subset fluidly coupled to and surrounding the interior subset by way of the set of channels; and a fluid delivery module surrounding the array and fluidly coupled to each well in the set of wells.

17 Claims, 11 Drawing Sheets

(51) Int. Cl.
 *B01L 3/00* (2006.01)
 *C12M 1/32* (2006.01)

(52) U.S. Cl.
 CPC .............. B01L 2300/0819 (2013.01); B01L 2300/0867 (2013.01); B01L 2400/0487 (2013.01); B01L 2400/086 (2013.01); C12M 23/12 (2013.01); G01N 2800/52 (2013.01)

(56) References Cited

U.S. PATENT DOCUMENTS

| | | |
|---|---|---|
| 4,710,635 A | 12/1987 | Chupp |
| 5,266,269 A | 11/1993 | Niiyama et al. |
| 5,491,343 A | 2/1996 | Brooker |
| 5,851,488 A | 12/1998 | Saul et al. |
| 5,883,370 A | 3/1999 | Walker et al. |
| 5,888,370 A | 3/1999 | Becker et al. |
| 5,993,630 A | 11/1999 | Becker et al. |
| 5,993,632 A | 11/1999 | Becker et al. |
| 6,016,712 A | 1/2000 | Warden et al. |
| 6,127,177 A | 10/2000 | Toner et al. |
| 6,133,030 A | 10/2000 | Bhatia et al. |
| 6,150,180 A | 11/2000 | Parce et al. |
| 6,174,683 B1 | 1/2001 | Hahn |
| 6,221,663 B1 | 4/2001 | Bhatia et al. |
| 6,228,624 B1 | 5/2001 | Terstappen |
| 6,281,008 B1 | 8/2001 | Komai et al. |
| 6,287,832 B1 | 9/2001 | Becker et al. |
| 6,365,362 B1 | 4/2002 | Terstappen et al. |
| 6,410,724 B1 | 6/2002 | Dejean et al. |
| 6,433,134 B1 | 8/2002 | Patron et al. |
| 6,525,997 B1 | 2/2003 | Narayanaswami et al. |
| 6,563,634 B2 | 5/2003 | Shimada et al. |
| 6,623,983 B1 | 9/2003 | Terstappen et al. |
| 6,641,708 B1 | 11/2003 | Becker et al. |
| 6,645,731 B2 | 11/2003 | Terstappen et al. |
| 6,692,952 B1 | 2/2004 | Braff et al. |
| 6,790,330 B2 | 9/2004 | Gascoyne et al. |
| 6,861,259 B2 | 3/2005 | Columbus |
| 6,960,449 B2 | 11/2005 | Wang et al. |
| 7,035,170 B2 | 4/2006 | Narayanaswami et al. |
| 7,172,866 B2 | 2/2007 | Hahn et al. |
| 7,198,901 B1 | 4/2007 | Rachlin |
| 7,217,520 B2 | 5/2007 | Tsinberg et al. |
| 7,238,521 B2 | 7/2007 | Hahn et al. |
| 7,258,990 B2 | 8/2007 | Falcovitz-Gerassi et al. |
| 7,266,777 B2 | 9/2007 | Scott et al. |
| 7,294,468 B2 | 11/2007 | Bell et al. |
| 7,316,897 B2 | 1/2008 | Bisconte De et al. |
| 7,332,288 B2 | 2/2008 | Terstappen et al. |
| 7,439,062 B2 | 10/2008 | Bhatt et al. |
| 7,449,558 B2 | 11/2008 | Yao et al. |
| 7,449,778 B2 | 11/2008 | Sander |
| 7,507,528 B2 | 3/2009 | Albert et al. |
| 7,595,157 B2 | 9/2009 | Tsinberg |
| 7,597,528 B2 | 10/2009 | Rodi |
| 7,604,777 B2 | 10/2009 | Columbus |
| 7,638,464 B2 | 12/2009 | Fagnani et al. |
| 7,695,956 B2 | 4/2010 | Tsinberg et al. |
| 7,763,704 B2 | 7/2010 | Ding et al. |
| 7,815,863 B2 | 10/2010 | Kagan et al. |
| 7,858,757 B2 | 12/2010 | Hollmann et al. |
| 7,863,012 B2 | 1/2011 | Rao et al. |
| 7,901,950 B2 | 3/2011 | Connelly et al. |
| 7,964,349 B2 | 6/2011 | Bell et al. |
| 8,008,032 B2 | 8/2011 | Forsyth et al. |
| 8,013,298 B2 | 9/2011 | Khursheed |
| 8,021,614 B2 | 9/2011 | Huang et al. |
| 8,103,080 B2 | 1/2012 | George et al. |
| 8,105,769 B2 | 1/2012 | Bell et al. |
| 8,105,780 B2 | 1/2012 | Su et al. |
| 8,131,053 B2 | 3/2012 | Ortyn et al. |
| 8,158,410 B2 | 4/2012 | Tang et al. |
| 8,175,371 B2 | 5/2012 | George et al. |
| 8,186,913 B2 | 5/2012 | Toner et al. |
| 8,293,524 B2 | 10/2012 | Ionescu-Zanetti et al. |
| 8,304,230 B2 | 11/2012 | Toner et al. |
| 8,329,422 B2 | 12/2012 | Rao et al. |
| 8,372,579 B2 | 2/2013 | Toner et al. |
| 8,372,584 B2 | 2/2013 | Shoemaker et al. |
| 8,406,498 B2 | 3/2013 | Ortyn et al. |
| 8,465,916 B2 | 6/2013 | Bell et al. |
| 9,145,540 B1 * | 9/2015 | Deutsch ............... C12M 23/10 |
| 2002/0119482 A1 | 8/2002 | Nelson et al. |
| 2002/0192808 A1 | 12/2002 | Gambini et al. |
| 2003/0138941 A1 | 7/2003 | Gong et al. |
| 2004/0106130 A1 | 6/2004 | Besemer et al. |
| 2004/0160599 A1 | 8/2004 | Hamamatsu et al. |
| 2004/0229349 A1 | 11/2004 | Daridon |
| 2004/0248318 A1 | 12/2004 | Weinberger et al. |
| 2005/0001176 A1 | 1/2005 | Loney et al. |
| 2005/0014201 A1* | 1/2005 | Deuthsch ............... G02B 21/34 435/7.2 |
| 2005/0118640 A1 | 6/2005 | Kureshy et al. |
| 2006/0128006 A1 | 6/2006 | Gerhardt et al. |
| 2007/0111302 A1 | 5/2007 | Handique et al. |
| 2007/0292837 A1* | 12/2007 | Deutsch ............... B01L 3/5085 435/4 |
| 2008/0014589 A1 | 1/2008 | Link et al. |
| 2008/0068588 A1 | 3/2008 | Hess et al. |
| 2008/0182273 A1 | 7/2008 | Hansen et al. |
| 2008/0206751 A1 | 8/2008 | Squirrell et al. |
| 2009/0061450 A1 | 3/2009 | Hunter |
| 2009/0081773 A1 | 3/2009 | Kaufman |
| 2009/0141593 A1 | 6/2009 | Taha |
| 2009/0153844 A1 | 6/2009 | Peter et al. |
| 2009/0317836 A1 | 12/2009 | Kuhn et al. |
| 2010/0120077 A1 | 5/2010 | Daridon |
| 2010/0210009 A1 | 8/2010 | Willson et al. |
| 2010/0261179 A1 | 10/2010 | Betley et al. |
| 2010/0304485 A1 | 12/2010 | Karnik et al. |
| 2010/0304978 A1 | 12/2010 | Deng et al. |
| 2011/0045994 A1 | 2/2011 | Voldman et al. |
| 2011/0117634 A1 | 5/2011 | Halamish et al. |
| 2011/0143964 A1 | 6/2011 | Zhou et al. |
| 2011/0227558 A1 | 9/2011 | Mannion et al. |
| 2012/0071355 A9 * | 3/2012 | Cooney ............... B01J 19/0046 506/16 |
| 2012/0129190 A1 | 5/2012 | Chiu et al. |
| 2012/0156675 A1 | 6/2012 | Lueerssen et al. |
| 2012/0164679 A1* | 6/2012 | Vrouwe ............... B01L 3/5027 435/29 |
| 2012/0194805 A1 | 8/2012 | Ness et al. |
| 2013/0244906 A1 | 9/2013 | Collins |
| 2014/0173443 A1 | 6/2014 | Hawkins et al. |
| 2015/0089359 A1 | 3/2015 | Brisebois |
| 2015/0093306 A1* | 4/2015 | Thorne ............... C12M 23/12 422/552 |
| 2015/0160931 A1 | 6/2015 | Glazer et al. |

OTHER PUBLICATIONS

Lindstrom, Sara (Royal Institute of Technology, Stockholm, Sweden, 2009, pp. 1-80).*
Guo, P. et al. Microfluidic capture and release of bacteria in a conical nanopore array. Lab Chip. vol. 12, p. 558-561, 2012, published online Nov. 2011.

* cited by examiner

Planar Broad Surface

Non-Planar Broad Surface

Non-Planar Broad Surface

SYSTEM FOR ISOLATING CELLS

CROSS-REFERENCE TO RELATED APPLICATIONS

This application claims the benefit of U.S. Provisional Application No. 61/829,537 filed on 31, May 2013, which is incorporated in its entirety by this reference.

TECHNICAL FIELD

This invention relates generally to the cell sorting field, and more specifically to a new and useful system and method for isolating and analyzing cells within the cell sorting field.

BACKGROUND

With an increased interest in cell-specific drug testing, diagnosis, and other assays, systems that allow for individual cell isolation, identification, and retrieval are becoming more desirable within the field of cellular analysis. Furthermore, with the onset of personalized medicine, low-cost, high fidelity cellular sorting systems are becoming highly desirable. However, preexisting cell capture systems suffer from various shortcomings that prevent widespread adoption for cell-specific testing. For example, flow cytometry requires that the cell be simultaneously identified and sorted, and limits cell observation to a single instance. Flow cytometry fails to allow for multiple analyses of the same cell, and does not permit arbitrary cell subpopulation sorting. Conventional microfluidic devices rely on cell-specific antibodies for cell selection, wherein the antibodies that are bound to the microfluidic device substrate selectively bind to cells expressing the desired antigen. Conventional microfluidic devices can also fail to allow for subsequent cell removal without cell damage, and only capture the cells expressing the specific antigen; non-expressing cells, which could also be desired, are not captured by these systems. Cellular filters can separate sample components based on size without significant cell damage, but suffer from clogging and do not allow for specific cell identification, isolation of individual cells, and retrieval of identified individual cells. Other technologies in this field are further limited in their ability to allow multiplex assays to be performed on individual cells, while minimizing sample preparation steps.

Thus, there is a need in the cell sorting field to create a new and useful cell system and method for isolating and analyzing cells.

BRIEF SUMMARY OF THE INVENTION

Not Applicable

DETAILED DESCRIPTION OF THE INVENTION

The following description of the preferred embodiments of the invention is not intended to limit the invention to these preferred embodiments, but rather to enable any person skilled in the art to make and use this invention.

1. System

Figure 1:
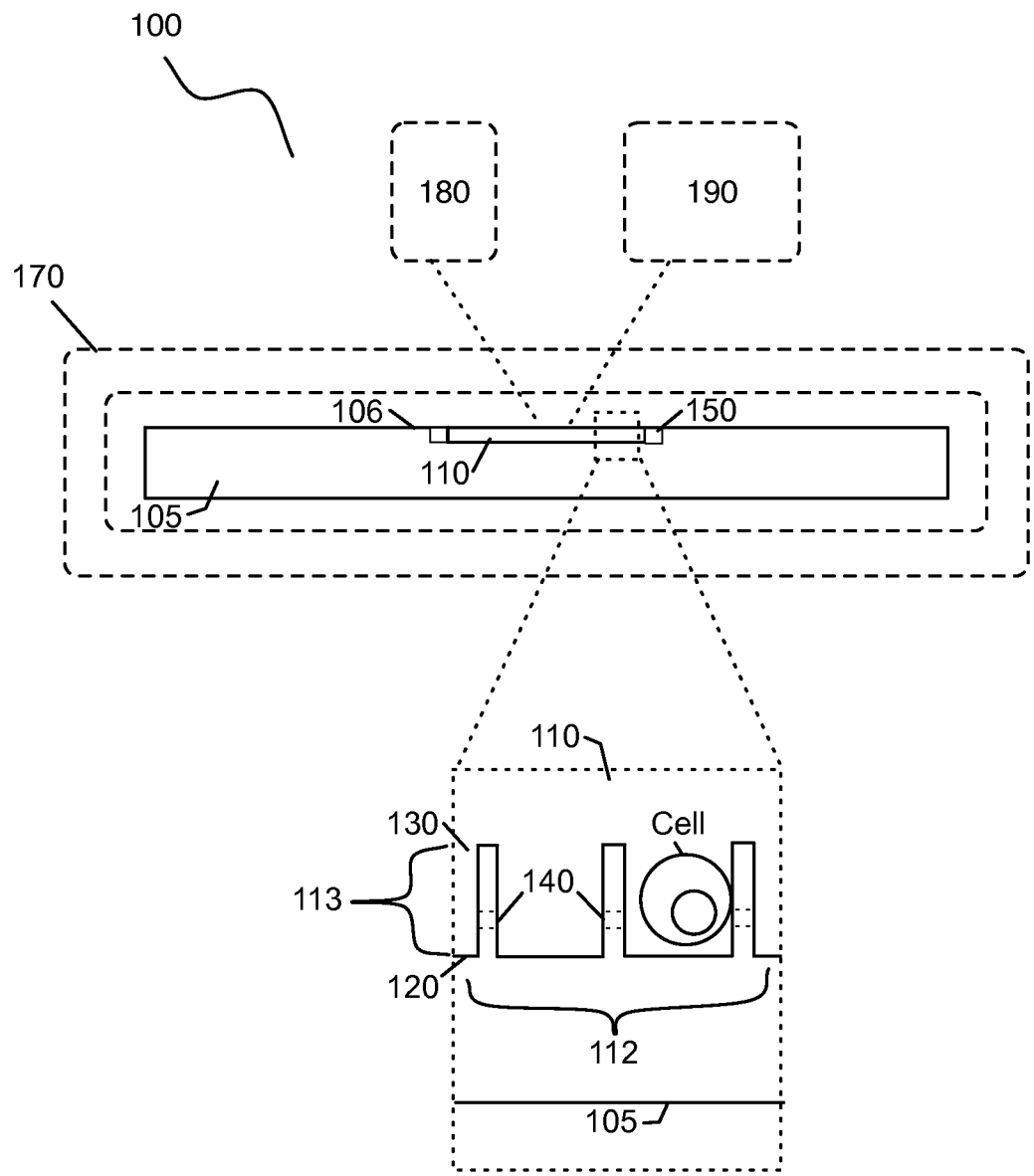
FIG. 1 is a schematic representation of an embodiment of a system for isolating and analyzing cells.

As shown in FIG. 1, a system 100 for isolating and analyzing a set of cells comprises: a substrate 105 having a broad surface; and an array 110 including a set of wells 112 defined at the broad surface of the substrate, each well 113 in the set of wells 112 including a base surface 120 defined within the substrate, an open surface 130 directly opposing the base surface 120, and a set of channels 140 that fluidly couple each well to every adjacent well in the set of wells. In some variations, the system 100 can further include a perimeter channel 150 surrounding the set of wells 112 and fluidly coupled to each well in an exterior subset 115 of the set of wells by way of at least one channel in the set of channels of each well in the exterior subset of the set of wells. To facilitate sample or fluid delivery to the array 110, the system 100 can further include a fluid delivery module 170 configured to couple to the substrate 105 and transfer a sample containing the set of cells and/or another fluid to the array 110. Additionally or alternatively, the system 100 can include a cell removal module 180 that extracts at least one of a single cell and a cell cluster from a well of the array. Additionally or alternatively, the system 100 can include an encapsulation module 190 configured to encapsulate the set of cells at the array 110, and facilitate delivery of reagents to encapsulated cells of the set of cells at the array 110.

The system 100 functions to isolate, capture, and retain cells of a cell population, in at least one of single-cell format and single-cluster format, at known, addressable locations, and further to facilitate performance of multiple single-cell assays that can be performed on individual cells (e.g., rare cells in a biological sample) or clusters of cells (e.g., doublets, triplets). Once cells are captured in defined locations determined by single cell capture wells, a fluidic network of the system 100 can be used to provide and deliver reagents simultaneously, sequentially, and/or in repetition to enable a variety of cellular, sub-cellular or molecular reactions to be performed in each of the single cells/cell clusters. The system 100 can also allow optical interrogation and detection of events on each of the captured cells at a single cell/single cluster level. The system 100 can additionally or alternatively enable selective release and/or selective removal of one or more of the captured cells for further processing and analysis. In some embodiments, the system 100 can confer the benefits of real-time cell tracking, viable cell retrieval, and selective downstream molecular analysis (e.g., electrophoresis), either in the same microfluidic chip or off-chip. In some embodiments, the system 100 can be used to capture circulating tumor cells (CTCs) and subpopulations of CTCs, such as circulating stem cells (CSCs), but can additionally or alternatively be used to capture any other suitable cell of possible interest. The system 100 is preferably defined on a substrate, more preferably a microfluidic chip, but can alternatively be located on or defined by any suitable substrate.

The system 100 preferably achieves individual cell capture and retention from a biological sample including a cell population, without antibody coated wells, and preferably maintains the viability of the cells throughout isolation, capture, retention, and/or removal. Furthermore, the system 100 is preferably configured to prevent undesired fluid currents that can lift cells from the substrate or move cells/cell clusters from wells at which the cells were initially captured. However, in some variations, the system 100 can be configured to facilitate moving of cells/cell clusters in any suitable manner. The flow path of a fluid (e.g., biological sample, process reagent) through the system 100 is preferably multi-directional and uniform, such that each cell/cell cluster in the system 100 experiences consistent conditions; however, the flow path can alternatively be unidirectional, bi-directional, or have any other suitable characteristic(s). Cell sorting and viability maintenance can additionally be accomplished by controlling the sample flow rate through the system, or through any other suitable means.

In operation, the system 100 preferably receives a biological sample including the cell population and facilitates distribution of the biological sample uniformly across the array 110 (e.g., using smearing, using a cytospin procedure, etc.). However, the system 100 can additionally or alternatively facilitate distribution of the biological sample across the array using positive pressure (e.g., positive pressure at an inlet to the array) and/or negative pressure (e.g., negative pressure at an outlet of the array). Additionally or alternatively, actuation pressure that facilitates sample distribution can be cycled in a pulse-width modulation fashion or sinusoidal fashion to provide net actuation pressure, either net positive at the inlet or net negative at the outlet. As such, desired cells having a defining characteristic (e.g., size-based characteristic, density-based characteristic, adhesion-based characteristic, etc.) can be trapped within a well 113 as the biological sample flows across the array 110. For example, in the variation of the system 100 configured to capture CTCs, the wells 113 are preferably configured based upon defining morpohological features of CTC cells, in order to facilitate capture and retention of CTCs in single cell or single cluster format. However, the system 100 can additionally or alternatively be configured to retain and facilitate processing or any other suitable particle of interest in any other suitable format.

1.1 System—Substrate

The substrate 105 has a broad surface 106, and functions to provide a medium at which the array 110 can be defined. The substrate 105 is preferably composed of a rigid material with high transparency (e.g., a transparent material, a translucent material), in order to facilitate imaging of the substrate 105 to analyze captured single cells/cell clusters. In a few such variations, the substrate 105 can be composed of any one or more of: glass, a silicone-based material, a polymer, and any other suitable material with high transparency. Alternatively, the substrate 105 can be composed of any other suitable material having any other suitable optical properties. In a few such variations, the substrate can be composed of any one or more of: a ceramic material, a semi-conducting material, a polymer, and any other suitable material. The substrate 105 composition can be configured to provide desired characteristics relating to any one or more of: mechanical characteristics (e.g., substrate mechanical properties as a mechanical stimulus), optical properties (e.g., transparency), electrical properties (e.g., conductivity), thermal properties (e.g., conductivity, specific heat, etc.), physical characteristics (e.g., wettability, porosity, etc.), and any other suitable characteristic. The substrate 105 can be processed using any one or more of: etching methods, molding methods, printing methods (e.g., 3D printing processes), machining methods, and any other suitable manufacturing processes suited to a brittle, elastic, or ductile substrate material.

Figure 2A:
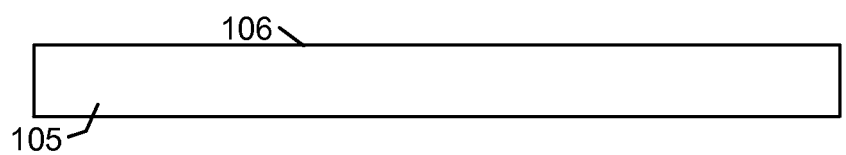
FIGS. 2A-2C depict variations of a portion of a system for isolating and analyzing cells.
Figure 2B:
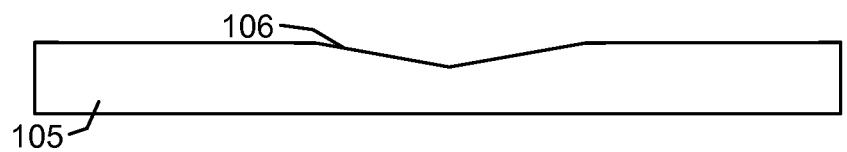
Figure 2C:

The broad surface 106 of the substrate 105 is preferably a planar surface, such that microfluidic elements of the system 100 are defined at least partially at a planar surface. Alternatively, the broad surface 106 of the substrate 105 can be a non-planar surface, as shown in FIG. 2A-2C, such that microfluidic elements of the system 100 are defined at least partially at a non-planar surface. In variations, the non-planar surface can be a concave surface, a convex surface, or a surface having concave, planar, and/or convex surfaces. Such variations can facilitate various methods of depositing and distributing a sample at the array 110. In any variations of the substrate 105 including a non-planar broad surface 106, the non-planar portion(s) are preferably shallow (e.g., having a small depth relative to a width of the broad surface) or short (e.g., having a small height relative to a width of the broad surface); however, the non-planar portion(s) can additionally or alternatively include portions that are deep (e.g., having a large depth relative to a width of the broad surface) or tall (e.g., having a large height relative to a width of the broad surface). In examples of a concave surface, the concave surface can be any one or more of a semi-spherical surface, a semi-cylindrical surface, a parabolic surface, a pyramidal surface, a conical surface, an ogive surface, a semi-ellipsoidal surface, and any other suitable surface. In examples of a convex surface, the convex surface can be any one or more of: semi-spherical surface, a semi-cylindrical surface, a parabolic surface, a pyramidal surface, a conical surface, an ogive surface, a semi-elliopsoidal surface, and any other suitable surface. In variations of the substrate 105 including a non-planar broad surface 106, the non-planar broad surface 106 preferably has a rotational axis of symmetry, for instance, to facilitate sample distribution by a cytospinning process. However, the surface can alternatively have any other suitable axis or type of symmetry, or can be asymmetrical. In any of these variations, the non-planar surface of the broad surface 106 can be produced by any one or more of: molding, by polishing, by spinning a material in a flow phase followed by setting the material, by machining, by printing (e.g., 3D printing), by etching, and by any other suitable process.

In a specific example, the array 110 is defined within a silicon mold using a three mask photolithographic process and deep reactive ion etching (DRIE) process to etch microfluidic elements into the silicon mold. In the specific example, the etched elements of the silicon mold are then transferred polymethylmethacrylate (PMMA) sheets as a substrate 105 using a hot embossing process. The substrate 105 in the specific example has dimensions of 3 inches by 1 inch, in order to substantially match dimensions of a glass microscope slide. In variations of the specific example, and/or for other variations of the array 110, hot embossing of cyclic olefin polymer (COP) can be substituted for PMMA to form the microfluidic structures of the array 110.

However, the substrate 105 can alternatively be any other suitable substrate 120 processed in any other suitable manner.

1.2 System—Array

The array 110 functions to capture the set of cells in addressable, known locations such that the set of cells can be individually identified, processed, and analyzed. As such, the array 110 is preferably configured to facilitate cell capture in at least one of single-cell format and single-cluster format. As shown in FIG. 1, the array 110 preferably includes a set of wells 112 defined at the broad surface 106 of the substrate 105, each well 113 in the set of wells 112 including a base surface 120 defined within the substrate, an open surface 130 directly opposing the base surface 120, and a set of channels 140 that fluidly couple each well to at least one adjacent well in the set of wells 112. In some variations, the array 100 can further include a perimeter channel 150 surrounding the set of wells 112 and fluidly coupled to each well 113 in an exterior subset 115 of the set of wells 112 by way of at least one channel in the set of channels 140 of each well in the exterior subset 115 of the set of wells. Each substrate 105 of the system 100 can have a single array 110, or can have multiple arrays 110 defined at the substrate in any suitable manner (e.g., in a radial configuration, in a rectangular configuration, in a linear configuration, in a curvilinear configuration, in a random configuration, etc.).

The set of wells 112 functions to receive the set of cells in at least one of single-cell format and single cluster format; however, the set of wells 112 can additionally or alternatively be configured to receive any other suitable type of particle, in any other suitable format. Each well 113 in the set of wells 112 is preferably identical to every other well in the set of wells 112, and includes a base surface 120 defined within the substrate 105, and an open surface 130 directly opposing the base surface 120, defined at the broad surface 106 of the substrate 105. The base surface 120 is preferably parallel to the open surface 130; however, in some variations, the base surface 120 can alternatively be non-parallel to the open surface 130. Similar to the broad surface 106 of the substrate 105, the base surface 120 can be a planar surface or a non-planar surface, and in variations of the base surface 120 having a non-planar surface, the non-planar surface can include convex and/or concave portions having any suitable geometric characteristic. Additionally or alternatively, the base surface 120 can be any one or more of: textured (e.g., to facilitate desired fluid flow behavior, to attract or repel a given particle type, etc.), characterized by a desired porosity, characterized by a desired surface treatment, and characterized by any other suitable feature that facilitates cell reception and/or retention in any other suitable manner.

Figure 3A:
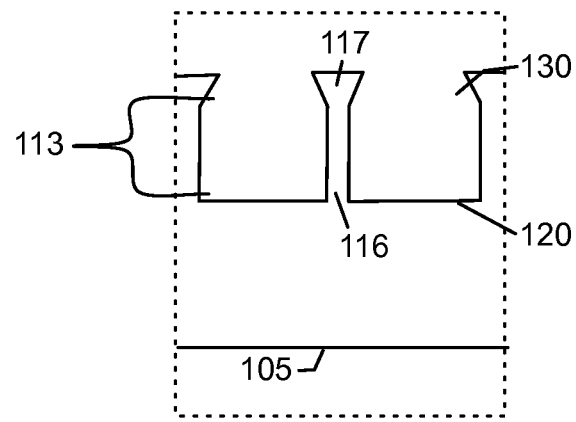
FIGS. 3A-3C depict variations of a portion of a system for isolating and analyzing cells.

The open surface 130 is preferably an opening in the substrate 105 that provides access to the base surface 120 of a well 113, and is configured to receive one of a single cell and a single cluster of cells from a direction perpendicular to the broad surface 106 of the substrate 105. As such, the open surface 130 can have a characteristic dimension (e.g., width, diameter) that is larger than, smaller than, or equal to that of the base surface 120. In an example for capture of circulating tumor cells (CTCs) from a sample in single-cell format, the characteristic dimension of either the base surface 120 or the open surface 130 can be 25 microns, and in variations of the example, the characteristic dimension(s) can have any dimension from 0.5 microns to 50 microns. In one example wherein the open surface 130 has a characteristic dimension smaller than that of the base surface 120, as shown in FIG. 3A, a well 113 can have a lip 117 that forms a boundary of the open surface 130 in order to provide a characteristic dimension that is smaller than that of the base surface 120. The lip 117 can be planar or non-planar, and can further facilitate retention of a single cell or a single cluster of cells at the well 113. The open surface 130 can, however, include any other suitable feature that facilitates cell reception and/or particle retrieval from the well 113 of the array 110.

Figure 3B:
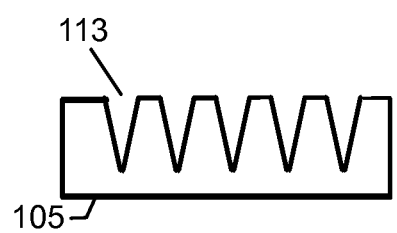
Figure 3C:
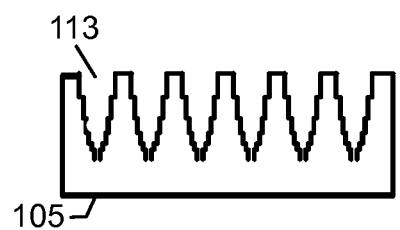

In relation to the base surface 120 and the open surface 130, each well 113 preferably has at least one wall 116 extending between the base surface 120 and the open surface 130, as shown in FIG. 3A, wherein the wall 116 at least partially separates the well 113 from at least one other adjacent well, defines a depth of the well, and is perpendicular to a plane defined by the open surface 130. The wall 116 can extend vertically from a plane defined by the open surface 130 to the base surface 120; as such, in some variations, a well 113 of the array 100 can be prismatic (e.g., cylindrical prismatic, polygonal prismatic, non-polygonal prismatic, etc.). However, the wall 116 can extend between the open surface 130 and the base surface 120 in any other suitable manner in other variations. For instance, the wall 116 can gradually reduces a characteristic dimension of the well from the open surface to the base surface (e.g., by forming steps, by gradually adjusting the characteristic dimension in a linear or a non-linear manner, etc.), examples of which are shown in FIGS. 3B and 3C. However, in some variations, a well 113 may not have a well-defined wall 116 perpendicular to a plane defined by the open surface 130 (e.g., the base surface may extend in some manner directly to the open surface without forming a wall perpendicular to the open surface). In examples, the base surface 120 and the open surface 130 can be separated, with or without a wall, by a distance of between 0.5 microns to 50 microns (e.g., 25 microns for an application involving capture of CTCs).

While every well 113 in the set of wells 112 can be substantially identical, the set of wells 112 can alternatively include wells that are non-identical to each other by any suitable feature (e.g., morphological feature, mechanical feature, surface coating feature, thermal conductivity feature, electrical conductivity feature, etc.). As such, some variations of the system 100 can be configured to capture at least one of multiple particle types and particles in multiple types of formats, in addressable locations, for processing and analysis. In a first example, the array 110 can include a first subarray 118 with wells having a first characteristic dimension (e.g., well diameter) in order to capture a first cell type in single cell format, and a second subarray 119 with wells having a second characteristic dimension (e.g., well diameter) in order to capture a second cell type in single cell format. In the first example, the first subarray 118 can be centrally located within the array 110, and the second subarray 119 can be peripherally located within the array 110 and have a second characteristic dimension that is smaller than the first characteristic dimension, in order to facilitate capture of larger particles at a central portion of the array 110 and smaller particles at a peripheral portion of the array 100 (e.g., in a cytospin application). In one variation of the first example, the array 110 can include wells having a gradient of characteristic dimensions in a radial direction (e.g., larger well dimensions toward the center of the array and smaller well dimensions toward the periphery of the array). In other variations of the first example, the array 110 can include wells having a gradient of any other suitable feature characteristic (e.g., morphological feature, mechanical feature, surface coating feature, thermal conductivity feature, electrical conductivity feature, etc.) in a radial direction. In other examples, the array 110 can include wells having a distribution (e.g., gradient) of any suitable feature characteristic (e.g., morphological feature, mechanical feature, surface coating feature, thermal conductivity feature, electrical conductivity feature, etc.) along any suitable direction (e.g., linear direction, radial direction, circumferential direction, etc.).

Figure 4A:
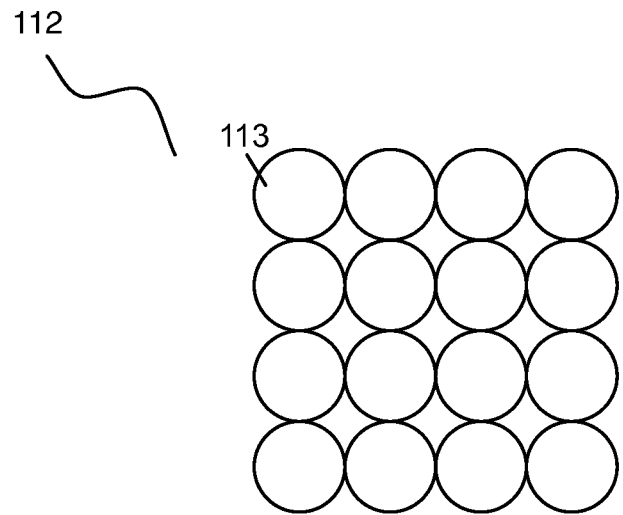
FIGS. 4A-4B depict example configurations of a portion of a system for isolating and analyzing cells.
Figure 4B:
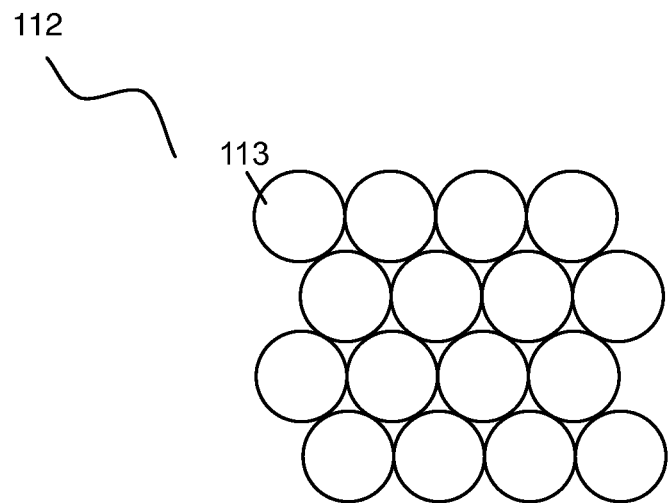

Furthermore, the set of wells 112 is preferably arranged in a packed array, but can alternatively be arranged in any other suitable manner. In one example, the set of wells 112 can be arranged in a packed rectangular array, as shown in FIG. 4A. In another example, the set of wells 112 can be arranged in a closest packed array (e.g., hexagonal closest packed array), as shown in FIG. 4B. In another example, the set of wells 112 can be arranged in any suitable irregular or non-uniform manner, for instance, to facilitate fluid flow from one portion of the array 110 to another portion of the array 110. However, the set of wells 112 can alternatively be arranged with any suitable spacing between wells (e.g., in a packed or a non-packed configuration), and in any other suitable manner.

Figure 5:
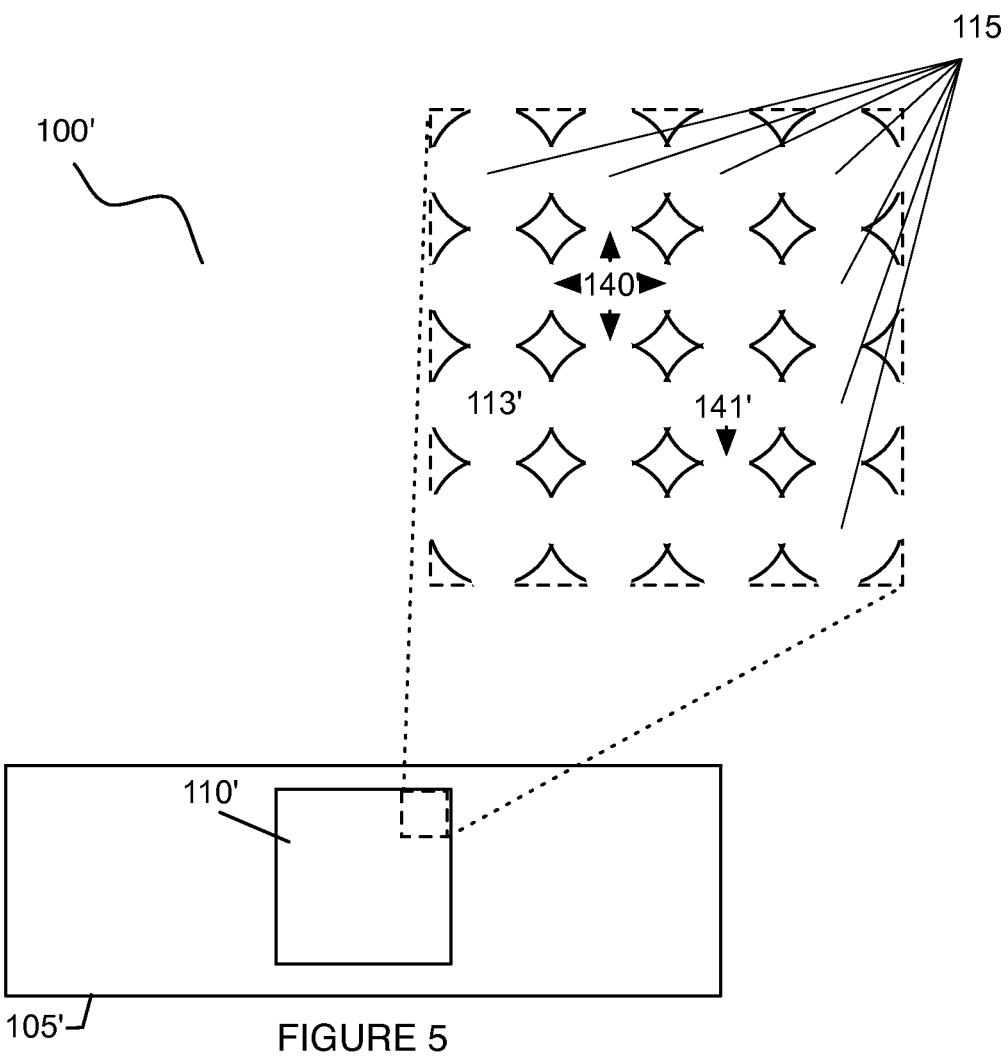
FIG. 5 depicts a specific example of a system for isolating and analyzing cells.

The set of channels 140 function to enable fluid flow exchange between at least two wells of the set of wells 112, and/or between one well of the set of wells 112 and another element of the system 100, while preventing migration of particle contents of a well 113 (e.g., a captured cell, a captured cell cluster). As such, a characteristic dimension (e.g., width, diameter) of each channel 141 in the set of channels 140 for a well 113 is preferably smaller than a characteristic dimension (e.g., width, depth) of the well 113 in order to enable retention of desired contents of a well 113. In some alternative variations, however, a well may be coupled to one or more channels having a characteristic dimension equal to or greater than that of a captured cell/cell cluster, in order to facilitate migration of a cell/cell cluster from one well to another well along a preferred direction. A channel 141 of a set of channels can extend from the open surface 130 of a well 113 to a base surface 120 of the well 113, such that a depth of the channel 141 is equal to the depth of the well 113. However, the channel(s) can alternatively have any other suitable depth (e.g., a depth less than that of the well) and be defined in relation to the open surface 130 and the base surface 120 of a well 113 in any other suitable manner. Preferably, every channel 141 in a set of channels 140 is identical, for a given well 113, in morphology (e.g., length, cross section); however, a set of channels 140 for a well 113 can alternatively include one or more non-identical channels 141 (e.g., a channel having a different length, a channel having a different cross section than other channels in a set of channels). The set of channels 140 can be arranged about a well 113 in a uniform radial pattern, can be arranged about a well 113 in a non-uniform radial pattern, or can be arranged about a well 113 in any other suitable manner to couple the well 133 to its adjacent well(s). However, in some variations, the set of channels 140 can be configured to couple each well to two adjacent wells (aside from an initial well and a terminal well, which would each only include a single channel), such that the set of wells 112 is coupled in series. In some variations, the channel(s) of a set of channels 140 can be defined within a region of the substrate 105 between adjacent wells, or can be defined by overlapping portions of adjacent wells, as shown in FIG. 5. In a specific example, a channel 141 can have a characteristic dimension of 5 microns, and in variations of the specific example, a channel 141, can have a characteristic dimension ranging from 0.5 microns to 50 microns. Alternatively, at least one well 113 in the set of wells 112 may not be coupled to every adjacent well in variations of the array 110. Furthermore, some variations of the array may not include a set of channels 140 for any well 113 of the set of wells 112.

Figure 6:
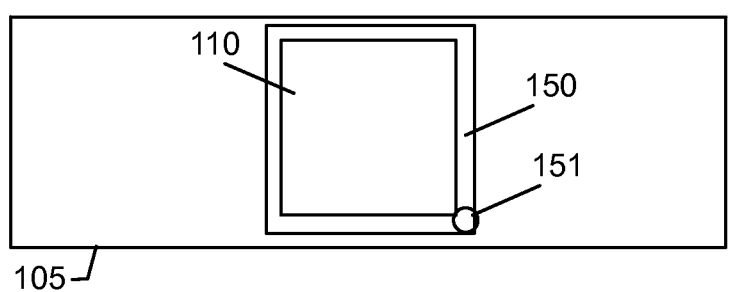
FIG. 6 depicts a variation of a system for isolating and analyzing cells.

As shown in FIGS. 1, 5, and 6, the system 100 can further include a perimeter channel 150 surrounding the set of wells 112 and fluidly coupled to each well 113 in an exterior subset 115 of the set of wells by way of at least one channel 141 in the set of channels 140 of each well in the exterior subset 115 of the set of wells 112. The perimeter channel 150 functions to enable modulation of an amount of fluid at the array 110, such that an amount of fluid within the array 110 can be reduced, maintained, or increased by way of the perimeter channel 150. As such, the perimeter channel 150 can receive and distribute process reagents throughout the array 110, and/or facilitate removal of excess or used process reagents from the array 110. The perimeter channel 150 can be at least partially enclosed by the substrate 105 or another element of the system 100, and coupled to a fluid port 151 that facilitates modulation of an amount of fluid at the array. As such, fluid can be delivered and/or removed from the array 110 by way of the fluid port 151, in an automatic or manual manner (e.g., using a pump, using capillary soaking, etc.). Additionally or alternatively, the perimeter channel 150 can include open portions not enclosed by the substrate 105 that facilitate fluid level modulation with or without use of the fluid port(s), for instance, using capillary soaking or evaporation. In some variations, the perimeter channel 150 can be coupled to any other suitable portion of the array 110 (e.g., a non-exterior subset of the array), in order to facilitate modulation of an amount of fluid at the array 110.

In some variations of the system 100, one or more wells of the array 110 can further include any other suitable element that facilitates stimulation and/or detection of a parameter (e.g., a cellular response parameter) at the well(s) of the array 110. In one example, one or more wells of the set of wells 112 of the array 110 can include an electrode embedded in the substrate 105 at a surface of the well 113 in order to facilitate detection of bioelectrical signals from contents of the well 113, and/or to facilitate stimulation of the contents of the well 113. In variations of the example, the electrode can be embedded with an exposed portion at least one of the base surface 120 and a wall 116 of the well 113. In other examples, the well(s) can be coupled to channels that facilitate delivery of process reagents to a cell/cell cluster at a well 113, or facilitate extraction of contents of a well 113 (e.g., processed intracellular contents) from the well 113. The system 100 can, however, include any other suitable element that facilitates processing and/or analysis of cells in at least one of single-cell format and single cluster format.

1.3 System—Fluid Delivery Module

Figure 7A:
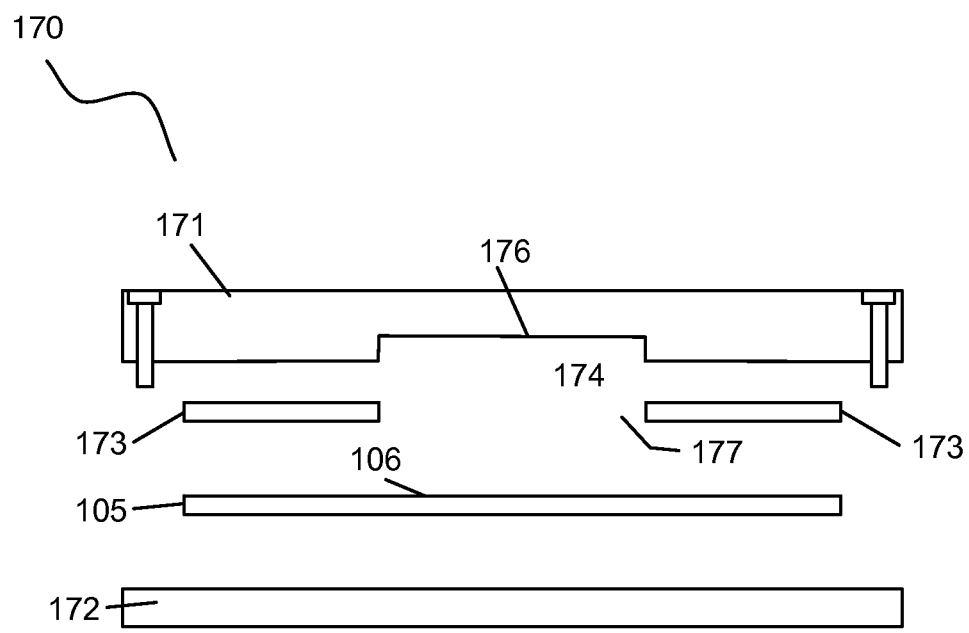
FIGS. 7A and 7B depict additional portions of an embodiment of a system for isolating and analyzing cells.
Figure 7B:
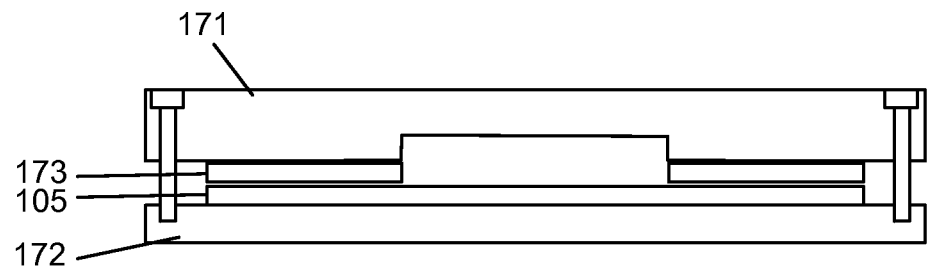

Also shown in FIGS. 1, 7A, and 7B, the system 100 can include a fluid delivery module 170 configured to couple to the substrate 105. The fluid delivery module 170 functions to transfer a sample containing the set of cells and/or another fluid to the array 110. As shown in FIGS. 7A and 7B, the fluid delivery module 170 can include a first plate 171 configured proximal the broad surface of the substrate 105, a second plate 172 configured proximal a surface of the substrate 105, directly opposing the broad surface of the substrate 105, and a clamping module configured to couple the first plate 171 to the second plate 172, thereby positioning and/or aligning the substrate 105 between the first plate 171 and the second plate 172. Alternatively, however, the first plate 171 can be directly coupled to the substrate 105 and/or to any other suitable element of the system 100, such that the fluid delivery module 170 omits a second plate 172.

As such, the fluid delivery module 170 facilitates positioning of the substrate 105 to receive and/or seal the sample or fluid at the array 110 (e.g., with a compressive force, with a hermetic seal, etc.). Additionally or alternatively, the fluid delivery module 170 can include an absorbant layer 173 configured between the first plate 171 and the substrate 105, that facilitates modulation of an amount of fluid at the array 110.

As shown in FIG. 7A, the first plate 171 can have a rectangular footprint that spans the broad surface 106 of the substrate 105. However, the first plate 171 can alternatively have any other suitable footprint (e.g., non-rectangular footprint, circular footprint, ellipsoidal footprint, etc.) configured to span all or a portion of the broad surface 106 of the substrate 105. The first plate 171 preferably has a recess 174 facing the broad surface 106 of the substrate 105, wherein the recess 174 functions as a reservoir to temporarily hold a sample and/or a processing reagent proximal to the array 110. As such, the recess 174 preferably spans the array 110, and aligns with the array when the first plate 171 is coupled to the substrate 105. In one variation, the recess 174 can be a rectangular recess defined within the surface of the first plate 171 facing the substrate 105. Furthermore, the recess can have a substantially planar base surface 176, as shown in FIG. 7A, or any other suitable base surface 176 (e.g., non-planar base surface). However, the recess 174 can alternatively have any other suitable morphology. Additionally or alternatively, the recess 174 can include a sealing element (e.g., o-ring, sealant, etc.) surrounding a region of the recess 174 proximal the substrate 105, in order to provide a hermetic seal upon coupling of the first plate 171 to the substrate 105. However, the first plate 171 can alternatively be configured in any other suitable manner.

The second plate 172 is configured proximal to a surface of the substrate 105, directly opposing the broad surface of the substrate 105, and functions to provide a base to which the first plate 171 can be coupled, thereby positioning the substrate 105 between the first plate 171 and the second plate 172. The second plate 172 preferably provides a complementary surface to which the surface of the substrate 105, opposing the broad surface 106, can be coupled. In one variation, the second plate 172 is a substantially planar, in order to provide a surface to which a planar surface of the substrate 105 (e.g., a planar surface directly opposing the broad surface of the substrate) can be coupled; however, the second plate 172 can be configured relative to the substrate 105 in any other suitable manner. Furthermore, the second plate 172 can include an aligning element that facilitates alignment of the second plate 172 relative to the substrate 105 and/or to the first plate 172. In variations, the aligning element can include any one or more of: a protrusion and/or a recess at the second plate 172 that facilitates alignment, a track that facilitates alignment, a magnetic element, and any other suitable alignment element.

In one variation, the first plate 171 is preferably coupled to the second plate with a coupling mechanism that can include one or more of: a pin, a screw, a magnetic coupler, a clamp, and any other suitable coupling mechanism. To prevent obstruction, the coupling mechanism can be located at peripheral portions of the system (e.g., at peripheral portions of the first plate 171, the second plate 172, and/or the substrate 105), or at any other suitable location that does not interfere with function of the substrate. Alternatively, some variations of the system 100 may omit the second plate 172, and have direct coupling between the first plate 171 and the substrate 105 in any suitable manner.

Some variations of the fluid delivery module 170 can include an absorbant layer 173 situated between the first plate 171 and the substrate 105. The absorbant layer 173 functions to facilitate modulation of an amount of fluid at the array 110, during a process that distributes the cells/cell clusters in single cell and/or cluster format at the array. As such, the absorbant layer 173 can be composed of any suitable absorbant material configured to absorb liquids, without receiving or retaining target cells of the sample. In some variations, the absorbant material can include any one or more of: a hydrogel having a network with pore sizes smaller than a characteristic dimension of a target cell, a porous material (e.g., a sponge), a hydrophilic material, and any other suitable absorbant material. Additionally or alternatively, in some variations, the absorbant layer 173 can be configured to attract, receive, and/or retain undesired particles from a sample, such that that the absorbant material facilitates filtration or segregation of undesired particles from the target particles of a sample. In such variations, the absorbant layer 173 can be configured to receive or retain undesired particles according to affinity molecule-based capture, pore size-based capture, adhesion behavior, and/or any other suitable mechanism.

As shown in FIG. 7A, the absorbant layer 173 is preferably a planar layer 173 in contact with both the first plate 171 and the substrate 105 upon coupling of the first plate 171 to align the recess 174 with the array 110. However, the absorbant layer 173 can alternatively have any other suitable morphology. Additionally, the absorbant layer 173 preferably has an opening 177 aligned with the recess 174 of the first plate 171, such that fluid within the reservoir formed by the recess 174 can reach the array 110 through the opening 177 of the absorbant layer 173. The opening can be a single opening, or can comprise any suitable number of openings that provide access between contents of the recess 174 and the array 110 of the substrate 110. However, the absorbant layer 173 can alternatively be configured in any other suitable manner.

Figure 8:
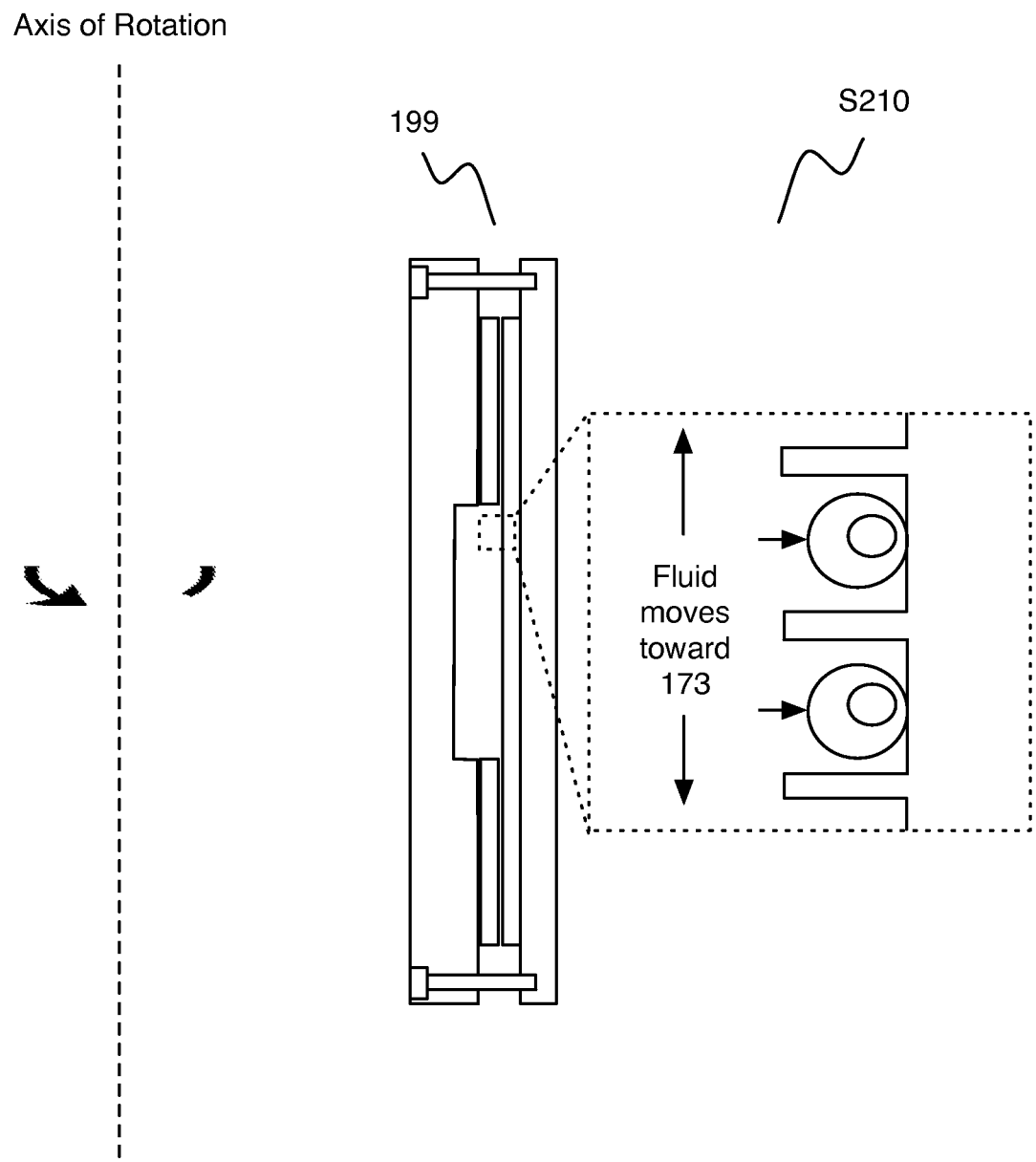
FIG. 8 depicts a variation of a process involving a system for isolating and analyzing cells.

In one example application, as shown in FIG. 8, an assembly 199 comprising the first plate 171, the absorbant layer 173, the substrate 105, and the second plate 172 can be coupled together and rotated about an axis of rotation parallel to and offset from the broad surface of the substrate 105, such that the normal defined by the broad surface 106 of the substrate 105 passes through the axis of rotation. As such, during rotation of the assembly 199, fluid within a reservoir formed by the recess 174 of the first plate 171 can be pushed toward the wells of the array 110 by centripetal force (e.g., to capture cells at the wells), while excess fluid can flow into the absorbant layer 173. However, in variations of the example application, the assembly 199 can be rotated about any other suitable axis, and/or capturing of cells at the array 110 can be performed in any other suitable manner.

1.4 System—Cell Removal Module

Figure 9:
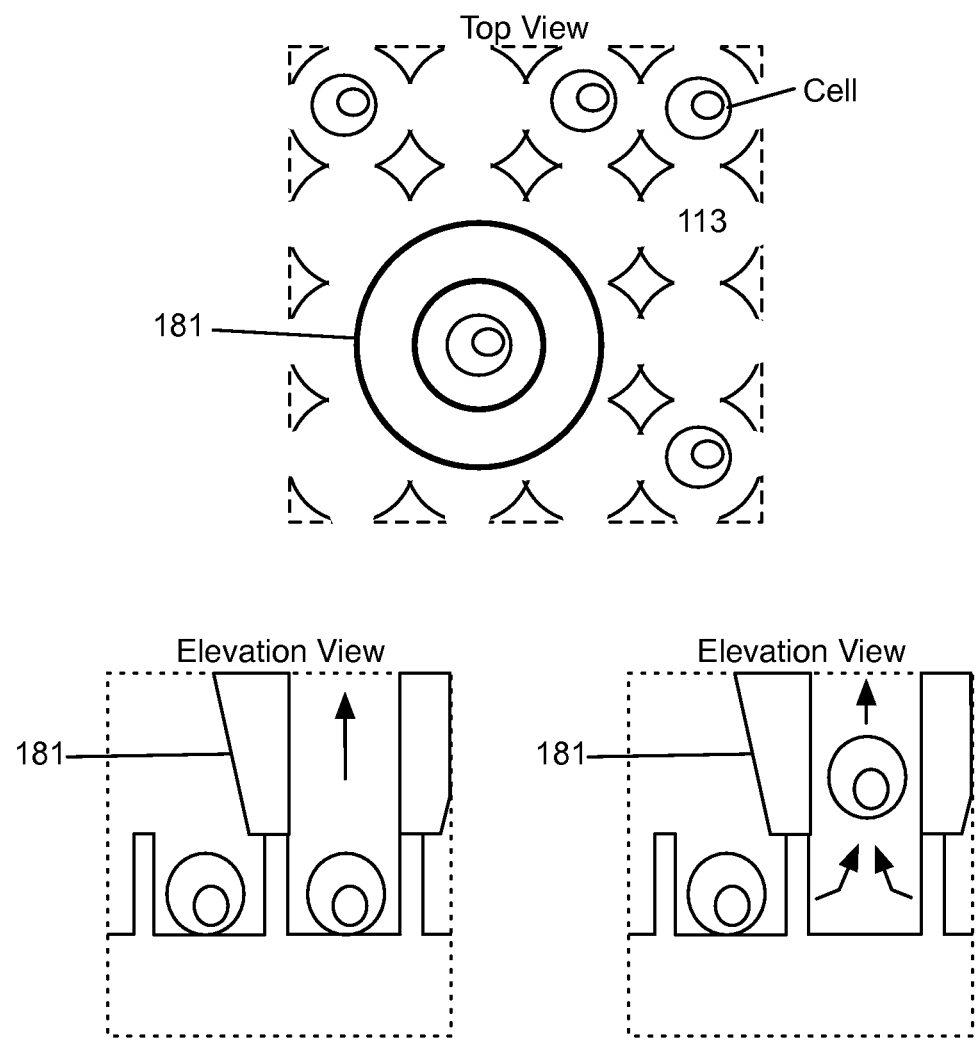
FIG. 9 depicts an additional portion of an embodiment of a system for isolating and analyzing cells.

Also shown in FIGS. 1 and 9, the system 100 can further include a cell removal module 180 that functions to extract at least one of a single cell and a cell cluster from a well 113 of the array. While an individual cell from a single well 113 is preferably selectively removed, the cell removal module 180 can facilitate simultaneous multiple cell/cell cluster removal from the array 110. The cell/cell cluster is preferably removed by applying a removal force to the cell. The removal force is preferably applied by aspirating the contents out of a well 113 (i.e., using a negative pressure); however, the removal force can additionally or alternatively be applied by pumping fluid through the array 110 (e.g., by way of a perimeter channel 150) to provide a positive pressure that drives the cell/cell cluster from the well 113. In one variation, the pump pressure provided by a pump mechanism at the cell removal module 180 is less than 10,000 Pa, and in a specific variation, the provided pump pressure is 6,000 Pa. However, any other suitable pump or aspiration pressure can be used.

In some variations, the cell removal module 180 can comprise a cell removal tool 181. The cell removal tool 181 functions to selectively remove one or more isolated cells from an addressable location within the system 100. The cell removal tool 181 is preferably configured to remove a cell/cell cluster from a single well 113, but can alternatively be configured to simultaneously remove multiple cells/cell clusters from multiple wells 113.

In a first variation of the cell removal tool 181, the cell removal tool 181 is configured to access the array 110 from a direction normal to the broad surface 106 of the substrate 105. The cell removal tool 181 preferably removes the cell/cell cluster in a substantially normal direction from the broad surface 106 of the substrate 105, but can alternatively remove the cell/cell cluster in an angled direction relative to the broad surface 106 of the substrate 105. The cell removal tool 181 preferably includes a hollow channel (e.g., of a micropipette) that accesses the array 110 and defines a substantially fluidly isolated volume in fluid communication with one or more wells. The hollow channel can include one or more sealing elements at the tip 182 (e.g., a polymeric coating or adequate geometry) that facilitate fluid seal formation with the well(s) 113. The cell removal tool 181 preferably tapers from a proximal end to the tip 181, in order to provide an adequate geometry to receive contents of a well 113 into the cell removal tool 181; however, the cell removal tool 181 can alternatively have any other suitable form. As such, the hollow needle is preferably configured to form a substantially fluidly isolated volume within a well 113 of interest, and a low-pressure generator (e.g., a pump) is then used to aspirate the retained cell/cell cluster out of the well 113, through the hollow channel, and into a cell collection volume of the cell removal tool 181. In one variation, the cell removal tool 181 is a micropipette having a height of 200 micrometers and a hollow channel diameter of 25 micrometers; however, other variations of the specific example can have any other suitable defining dimensions.

The cell removal tool 181 can be manufactured using microfabrication techniques, or can additionally or alternatively be injection molded, laser cut, stamped, or manufactured using any other suitable manufacturing technique. In one variation of hollow needle manufacture, a lumen is preferably etched into a substrate 110, such as silicon, using etching techniques such as deep reactive ion etching (DRIE), plasma etching, or any other suitable etching method. This step is preferably utilized with a mask that covers the portions of the substrate 110 to be protected. The walls and associated profiles are then preferably manufactured through isotropic etching of the substrate 110 utilizing a corrosive liquid or plasma, but any other suitable isotropic material removal method can be used. A mask is preferably used to protect the puncture end. Multiple hollow needles are preferably simultaneously manufactured as an array 200, but can alternatively be individually manufactured. The cell removal tool 181 can, however, comprise any other suitable cell removal tool such as that described in U.S. application Ser. No. 13/557,510, entitled "Cell Capture System and Method of Use" and filed on 25, Jul. 2012, which is herein incorporated in its entirety by this reference.

Cell removal from the system 100 is preferably automated, but can additionally or alternatively be semi-automated or manual. Furthermore, cell removal can be performed along with cell identification, comprising automatic fixing, permeabilization, staining, imaging, and identification of the cells removed from the array 110 through image analysis (e.g., through visual processing with a processor, by using a light detector, etc.) or in any other suitable manner. The cell removal module 180 can be configured to facilitate advancement of a cell removal tool 181 to a well 113 containing a cell/cell cluster of interest, for instance, with an actuation subsystem. The cell removal module 180 can additionally or alternatively be configured to facilitate cell removal method selection and/or cell removal tool selection. In another variation, cell identification at the cell removal module 180 can be semi-automated, and cell retrieval can be automated. For example, cell staining and imaging can be done automatically, wherein identification and selection of the cells of interest can be done manually. In another variation, all steps can be performed manually. However, any combination of automated or manual steps can be used.

1.5 System—Encapsulation Module

Additionally or alternatively, the system 100 can include an encapsulation module 190 configured to encapsulate the set of cells at the array 110, and facilitate delivery of reagents to encapsulated cells of the set of cells at the array 110. In one variation, the encapsulation module 190 can include a first encapsulation layer 191 coupled to the substrate 105 proximal the broad surface 106 of the substrate 105, that functions to seal cells captured at the set of wells 112 within an encapsulation matrix 199. As such, the first encapsulation layer 191 can form a boundary opposing the base surfaces 120 of each well 113 in the set of wells 112. The first encapsulation layer 191 is preferably an optically clear laminate, in order to facilitate visualization of contents of the array 110; however, the first encapsulation layer 191 can alternatively comprise any other suitable material. Furthermore, the first encapsulation layer 191 can be reversibly removed and/or applied to the array 110, in order to facilitate access to encapsulated contents of the set of wells 112.

Figure 10:
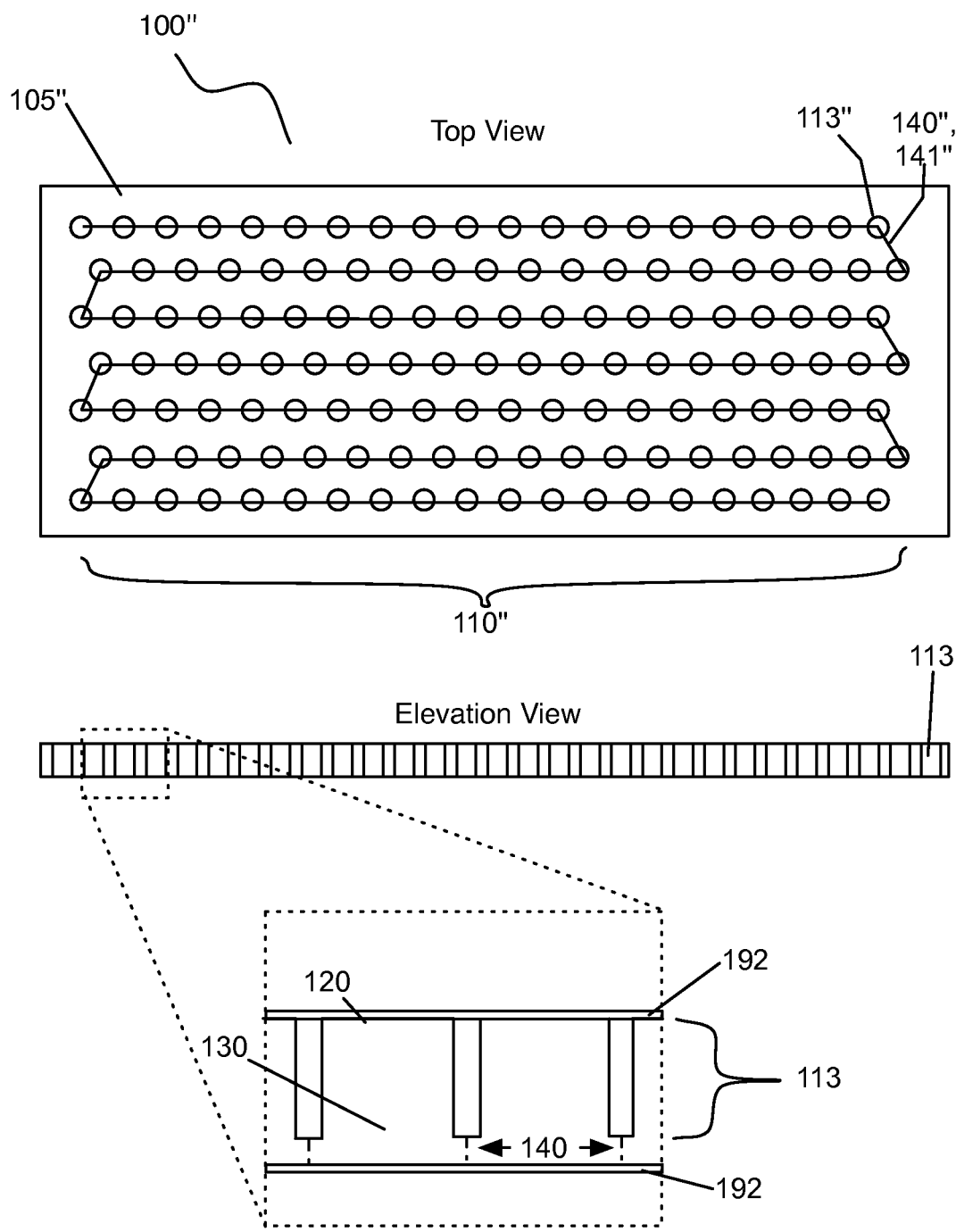
FIG. 10 depicts a specific example of a system for isolating and analyzing cells.
Figure 11:
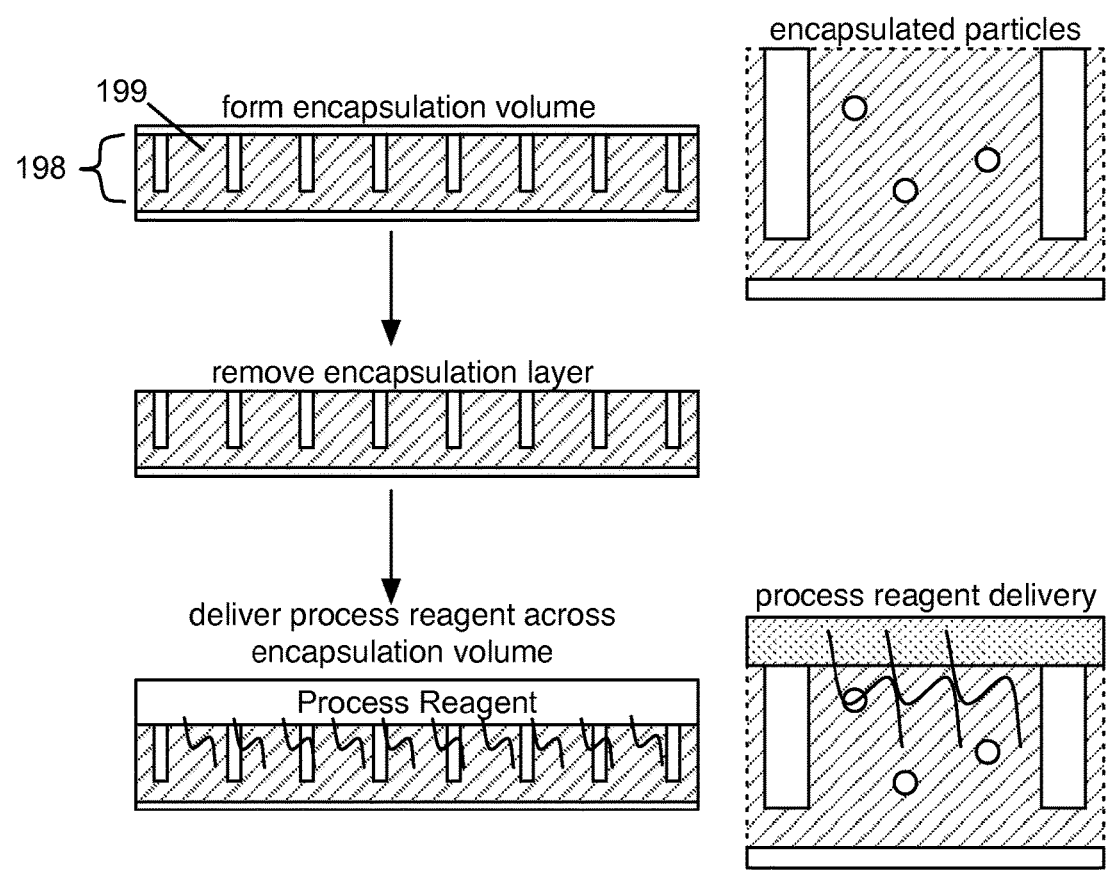
FIG. 11 depicts an additional portion of an embodiment of a system for isolating and analyzing cells.

In one variation, as shown in FIGS. 10 and 11, an encapsulation matrix 199 can be flowed into the array 110 with the encapsulation module 190 at any suitable portion of the array 110, forming an encapsulation volume 198 spanning the set of wells 112 and the set of channels 140 for each well 113 in the set of wells 112, up to the first encapsulation layer 191. The encapsulation matrix 199 preferably isolates a well 113 within an array 110. The encapsulation matrix 501 preferably has a flow state and a set state, wherein any one or more of: a photochemical reaction, phase transition, thermochemical reaction, polymerization reaction and any other suitable reaction switches the encapsulation matrix 199 from the flow state to the set state. In the flow state, the encapsulation matrix 199 is preferably substantially viscous, such that the encapsulation matrix 199 does not flow into the wells 113 during introduction into the system 100. In the set state, the encapsulation matrix 199 is preferably a solid or gel that prevents particle egress from the wells 113 (e.g., egress of cells and/or large nucleic acid molecules from the pores), and is preferably porous or selectively permeable to permit small molecule, buffer, and reagent penetration therethrough. In one variation, the encapsulation matrix 199 is a microporous agarose gel, and in another variation, the encapsulation matrix 199 is a photopolymerizable hydrogel, such as PEG or polyacrylamide with photoinitiator; however, the encapsulation matrix 199 can alternatively be any suitable material with any other suitable polymerization agent.

In some variations, the encapsulation module 190 can additionally include a second encapsulation layer 192 forming the base surfaces 120 of the set of wells 112 of an array, such that the base surfaces 120 are not directly defined within the substrate 105, but at the second encapsulation layer 192. As such, the second encapsulation layer 192 can form a second boundary defining the base surfaces 120 of each well 113 in the set of wells 112, thereby partially bounding the encapsulation volume 198. The second encapsulation layer 192 is preferably an optically clear laminate, in order to facilitate visualization of contents of the array 110; however, the second encapsulation layer 192 can alternatively comprise any other suitable material. Furthermore, the second encapsulation layer 192 can be reversibly removed and/or applied to the array 110, in order to facilitate access to encapsulated contents of the set of wells 112.

Preferably, as shown in FIGS. 10 and 11, the encapsulation module 190 is configured such that diffusion of one or more reagents through the encapsulation volume 198 occurs upon removal of the second encapsulation layer 192 (e.g., in a direction from the base surface of a well toward the open surface of the well) from the substrate 105; however, the encapsulation module can additionally or alternatively be configured such that diffusion of one or more reagents through the encapsulation volume 198 occurs upon removal of the first encapsulation layer 191 (e.g., in a direction from the open surface of the well toward the base surface of the well) from the substrate 105. As such, removal of one or both of the first encapsulation layer 191 and the second encapsulation layer 192 from the substrate 105 can provide access of one or more reagents, through the encapsulation matrix 199, to captured contents at the set of wells 112. In examples, such processing reagents can include any one or more of: stains (e.g., cell-specific stains), cocktails (e.g., antibody cocktails), lysing reagents, fixing reagents, permeabilization reagents, culture reagents (e.g., media), and any other suitable process reagent. The reagent(s) can be delivered through the encapsulation volume 198 by applying pressure (e.g., positive pressure, negative pressure) and/or by passive diffusion. However, the encapsulation module 190 can alternatively be configured in any other suitable manner.

1.6 System—Specific Examples

In a first specific example, as shown in FIG. 5, the system 100' includes an array 110' of 250,000 wells arranged in an rectangular packed array, wherein each well 113' is coupled to every adjacent well by a fluid channel formed at the overlap between adjacent wells. In the first specific example, each well in the array 110' has a diameter of 25 microns (e.g., a circumscribed diameter) and a depth of 25 microns, as defined between the base surface 120 and the open surface 130 of each well 113'. The array 110' of the first specific example can receive a sample volume from 0.1 to 10 milliliters in volume; however, other variations of the first specific example can receive any other suitable sample volume. In the first specific example, every fluid channel 141' of a set of fluid channels 140' for each well 113' has a width of 5 microns, in order to enable cell/cell cluster retention, while allowing fluid exchange. In the first specific example, the substrate 105' is coupled between a first plate 171 and a second plate 172, with an absorbant layer 173 situated between the first plate 171 and the substrate 105'. The absorbant layer has a rectangular opening 177 aligned with a rectangular recess 174 of the first plate 171, in order to facilitate fluid flow from a reservoir formed by the recess 174 through the opening 177. Other variations of the first specific example can, however, include any other suitable elements that facilitate cell/cell cluster capture, retention, processing, sorting, and/or analysis in any other suitable manner.

In a second specific example, as shown in FIG. 10, the system 100" includes an array 110" of 414 wells 113" arranged in series, wherein each well 113" (aside from an initial well and a terminal well) is coupled to two adjacent wells in series by fluid channels 141" defined at regions between adjacent wells. In the second specific example, the initial well and the terminal well are each only coupled to one adjacent well in the set of wells 112 by way of fluid channels 141". In the second specific example, the set of wells 112 is arranged in a boustrophedonic pattern, but variations of the second specific example can include arrangement of the set of wells 112 in any other suitable manner (e.g., serpentine pattern, spiral pattern, linear pattern, curvilinear pattern, etc.). In the second specific example, each well in the array 110" has a diameter of 1.1 millimeters (e.g., a circumscribed diameter) and a depth of 1 millimeter, as defined between the base surface 120 and the open surface 130 of each well 113", in order to define an approximately 1 milliliter volume capacity for each well. In the second specific example, every fluid channel 141" of a set of fluid channels 140" for each well 113" has a cross section of 250 microns×250 microns, and is configured proximal the open surfaces 130" of the set of wells 112, in order to enable cell/cell cluster retention, while allowing fluid exchange. Furthermore, in the second specific example, a well 113" is spaced from an adjacent well in the set of wells 112" by a spacing of 2 millimeters. In the second specific example, the substrate 105" is coupled between a first encapsulation layer 191 and a second encapsulation layer 192, each comprising an optically clear laminate, and wherein the second encapsulation layer 192" forms the base surfaces 120 of the set of wells 112. Upon delivery of an encapsulation matrix 199 into the array 110" and transitioning of the encapsulation matrix 199 to a set state, the second encapsulation layer 192 of the encapsulation module 190 is removed to allow passive diffusion through the encapsulation matrix 199 and to encapsulated contents of the set of wells 112. Other variations of the first specific example can, however, include any other suitable elements that facilitate cell/cell cluster capture, retention, processing, sorting, and/ or analysis in any other suitable manner.

Additionally or alternatively, the system 100 can include any other suitable element that facilitates cell processing and/or analysis. For instance, the system 100 can include optical elements (e.g., embedded within the substrate 105, coupled to the substrate 105) that function to facilitate imaging. The optical elements function to adjust incoming light, preferably to facilitate imaging. The optical elements can function to bend, reflect, collimate, focus, reject, or otherwise adjust the incoming light. The optical elements are preferably defined within the substrate 105, but can alternatively be defined by any other suitable component of the system 100. Optical elements can include any one or more of: light reflectors disposed within the substrate thickness adjacent the array(s) 110 defined on a surface of the substrate 105 opposite that defining the array 110, microlenses defined on a broad surface of the substrate 105 proximal that defining the array 110, light collimators, light polarizers, interference filters, light reflectors (e.g., 90° illumination elements), elements that minimize excitation rays from going into path of collected fluoresence emission light, diffraction filters, light diffusers, and any other suitable optical element. The system 100 can additionally or alternatively include well affinity mechanisms that function to attract a cell of interest 10 towards a well 113. Well affinity mechanisms can include electric field traps, affinity moieties (e.g., coated to a well surface), features (e.g., microfluidic features) that direct flow into an element, or any other suitable pore affinity mechanism. The system 100 can, however, include any other suitable element(s).

Additionally, as a person skilled in the field of cell sorting will recognize from the previous detailed description and from the figures and claims, modifications and changes can be made to the embodiments, variations, examples, and specific applications of the system 100 described above without departing from the scope of the system 100.

2. Method

Figure 12:
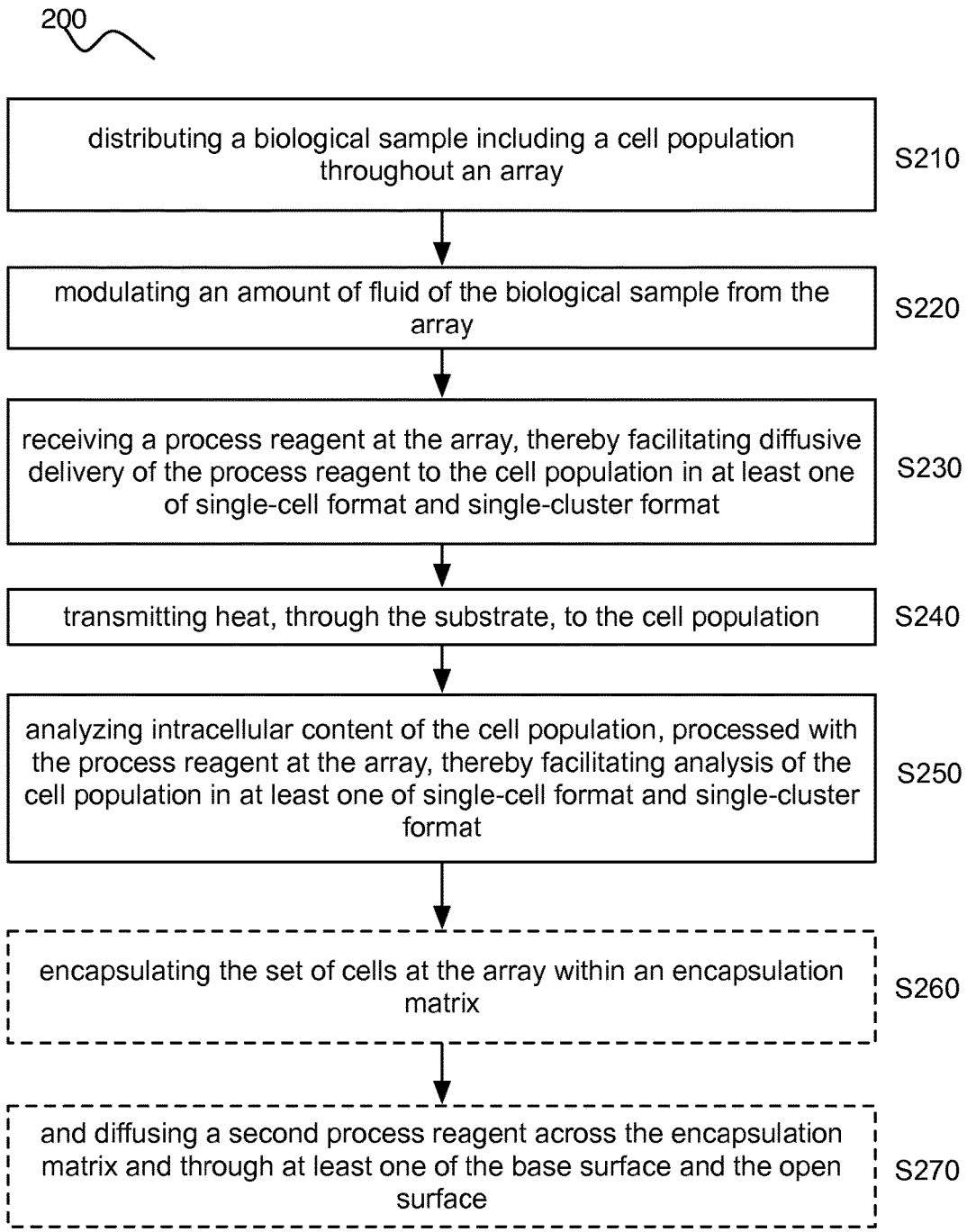
FIG. 12 depicts a schematic representations of an embodiment of a method for isolating and analyzing cells.

As shown in FIG. 12, a method 200 for isolating and analyzing a set of cells comprises: distributing a biological sample including a cell population throughout an array comprising a set of wells defined at the broad surface of a substrate, each well of the set of wells including a base surface, an open surface directly opposing the base surface, defined at the broad surface of the substrate, and configured to retain one of a single cell and a single cluster of cells of the cell population, and a set of channels that fluidly couple each well to at least one adjacent well in the set of wells S210; modulating an amount of fluid of the biological sample from the array S220; receiving a process reagent at the array, thereby facilitating diffusive delivery of the process reagent to the cell population in at least one of single-cell format and single-cluster format S230; transmitting heat, through the substrate, to the cell population S240; and analyzing intracellular content of the cell population, processed with the process reagent at the array, thereby facilitating analysis of the cell population in at least one of single-cell format and single-cluster format S250. The method 200 can additionally or alternatively include any one or more of: encapsulating the set of cells at the array within an encapsulation matrix S260; and diffusing a second process reagent across the encapsulation matrix and through at least one of the base surface and the open surface S270.

The method 200 functions to enable isolation, capture, and retention of cells, more preferably cells in single-cell format and/or single-cluster format, at known, addressable locations, and further to facilitate performance of multiple single-cell/single cluster assays that can be performed on individual cells or cell clusters (e.g., rare cells in a biological sample). The method 200 is preferably implemented at least in part using the system 100 described in Section 1 above; however the method 200 can additionally or alternatively be implemented using any other suitable system 100 for cell capture and analysis. In some embodiments, the method 200 can be used to capture and facilitate analyses of circulating tumor cells (CTCs) and subpopulations of CTCs, such as circulating stem cells (CSCs), but can additionally or alternatively be used to capture any other suitable cell of possible interest for processing and analysis.

Block S210 recites: distributing a biological sample including a cell population throughout an array comprising a set of wells defined at the broad surface of a substrate, each well of the set of wells including a base surface, an open surface directly opposing the base surface, defined at the broad surface of the substrate, and configured to retain one of a single cell and a single cluster of cells of the cell population, and a set of channels that fluidly couple each well to at least one adjacent well in the set of wells. Block S210 functions to receive a biological sample including target cells of interest at an embodiment of the system 100 described in Section 1 above, and to facilitate distribution of the target cells into wells of the system 100 in at least one of single-cell format and single-cluster format. However, Block S210 can alternatively include receiving a biological sample at any other suitable system configured to capture cells in at least one of single-cell format and single-cluster format. In variations of Block S210, the biological sample can be received directly at a variation of the array (e.g., by pipetting, by fluid delivery through a fluid channel coupled to the array), at the array by way of a variation of the first plate of a fluid delivery module (e.g., from a reservoir defined by a recess of the first plate, from a fluid channel coupled to the first plate, from a fluid channel embedded within the first plate and in fluid communication with the array, etc.), and/or in any other suitable manner. Furthermore, in variations of Block S210, the cell population can include a cell population of target cells (e.g., CTCs, CSCs) and/or any other suitable particle of interest.

In variations of Block S210, distributing can include any one or more of: cytospinning the substrate with the biological sample about an axis parallel to the broad surface of the substrate, cytospinning the substrate with the biological sample about an axis perpendicular to the broad surface of the substrate, cytospinning the substrate with the biological sample about an axis oriented at any suitable angle relative to the broad surface of the substrate, smearing the biological sample at the array of the substrate, depositing the biological sample at the array under positive and/or negative pressure (e.g., by way of a pumping mechanism), incubating the biological sample at the array for a period of time, and in any other suitable manner of sample deposition and distribution. Furthermore, in applications of Block 5210 including cytospinning, an axis of rotation can be offset from any suitable reference point of the substrate, in any suitable manner. In one specific application, as shown in FIG. 8, Block S210 includes rotating an assembly comprising a first plate coupled to a second plate and with the substrate and an absorbant layer between the first plate and the second plate, about an axis of rotation parallel to and offset from the broad surface of the substrate, such that the normal defined by the broad surface of the substrate passes through the axis of rotation. As such in the specific example, during rotation of the assembly, fluid within a reservoir formed by a recess of the first plate can be pushed toward the wells of the array by centripetal force (e.g., to capture cells at the wells), while excess fluid can flow into the absorbant layer. In the specific application, the assembly is rotated at an angular velocity from 500-2000 revolutions per minute; however, other variations of the specific application can include rotation of any other suitable assembly at any other suitable angular velocity. Furthermore, in variations of the specific application, the assembly can be rotated about any other suitable axis, and/or capturing of cells at the array can be performed in any other suitable manner.

Block S220 recites: modulating an amount of fluid of the biological sample at the array, which functions to increase, decrease, or maintain an amount of fluid, from the biological sample, at the array, thereby facilitating capture of cells at the array in at least one of single-cell format and single-cluster format. Block S220 preferably includes reducing an amount of fluid at the array; however, Block S220 can additionally or alternatively include increasing or maintaining an amount of fluid at the array. In variations, Block S220 can include modulating the amount of fluid by any one or more of: applying negative and/or positive pressure at the array (e.g., at a pump coupled to the system 100), using capillary soaking, by evaporation (e.g., using a heating element of the system, by passive evaporation), and any other means of modulating an amount of fluid at the array.

In one variation, Block S220 can include providing an absorbant layer at the array, configured to absorb excess fluid at the array by capillary soaking. In a specific example of this variation, the absorbant layer can include an opening aligned with the array, as described in Section 1 above, wherein cytospinning of a substrate including the array simultaneously forces cells into the set of wells of the array in at least one of single-cell format and single-cluster format and facilitates flow of excess fluid into the absorbant layer. As such, in some variations, Block S220 can be performed simultaneously with Block S210 (e.g., in cytospinning applications), or can alternatively be performed prior to or after Block S210.

Block S230 recites: receiving a process reagent at the array, thereby facilitating diffusive delivery of the process reagent to the cell population in at least one of single-cell format and single-cluster format. The process reagent can include any one or more of: a lysing reagent, a fixing reagent, a permeabilization reagent, a stain, a reagent for immunochemistry, a reagent for an in-situ hybridization assay (e.g., a fluorescence in-situ hybridization assay, FISH) for nucleic acids (e.g., DNA, RNA, mRNA, etc.), a reagent for polymerase chain reaction (PCR), a culture reagent (e.g., media) for cell maintenance and/or subsequent harvesting from the array, and any other suitable reagent. In variations, the process reagent(s) can be delivered to and distributed across the array in a manner similar to that of distributing the biological sample at the array in variations of Block S210. Additionally or alternatively, the amount(s) of the process reagent(s) at the array can be modulated in a manner similar to that of modulating fluid as in variations of Block S220. However, receiving the process reagent(s) and/or modulating the amount(s) of the process reagent(s) can additionally or alternatively be performed in any other suitable manner.

Block S240 recites: transmitting heat, through the substrate, to the cell population captured at the array, which functions to provide controlled incubation and/or thermocycling of the cell population with the process reagent(s) received in variations of Block S230. Block S240 preferably includes providing uniform heating at each well of the set of wells of the array; however, Block S240 can alternatively include providing heat non-uniformly across the array (e.g., providing heat with a gradient to examine effects of different heating parameters on the cell population). In variations, Block S240 can include contacting the substrate with at least one heating element, adjusting an environmental temperature of the substrate, or transmitting heat throughout the substrate by way of heating elements coupled to or embedded within the substrate. However, transmitting heat through the substrate can additionally or alternatively be performed in any other suitable manner. Transmitting heat thus includes incubating the substrate, with the cell population and a process reagent for a desired amount of time at a desired temperature, according to parameters suited for the process reagent(s) provided in Block S230. As such, transmitting heat can facilitate one or more of: lysing the cell population, fixing the cell population, permeabilizing the cell population, staining the cell population, performing immunochemistry for the cell population, binding a probe to intracellular nucleic acid content of the cell population, as in an in-situ hybridization assay (e.g., a fluorescence in-situ hybridization assay, FISH), performing polymerase chain reaction for nucleic acid content of the cell population, culturing the cell population, and any other suitable application.

In variations of the method 200, Blocks S220, S230, and/or S240 can be performed with any suitable number of repetitions, according to protocols for processing the cell population according to different assays. For instance, removing excess fluid can be performed prior to and/or after heating the substrate, in order to remove excess process reagent(s) from the array after they are no longer needed. Furthermore, Blocks S220, S230, and/or S240 can be performed in any suitable order or simultaneously, according to protocols for processing the cell population according to different assays.

Block S250 recites: analyzing intracellular content of the cell population, processed with the process reagent at the array, thereby facilitating analysis of the cell population in at least one of single-cell format and single-cluster format. In variations, Block S250 can include any one or more of: harvesting contents of the set of wells (e.g., cells, intracellular content), culturing cells captured at the set of wells, detecting biomarkers exhibited by the cell population (e.g., using fluorescent detection), performing a quantitative analysis (e.g., a quantitative analysis of mRNA expression), characterizing a cell phenotype (e.g., a cancer cell phenotype) based upon biomarker expression, providing a recommended therapy based upon characterization of a cell phenotype, performing flow cytometry with captured cells of the cell population, and performing any other suitable analysis. The analyses performed in variations can thus be performed for cells within and/or harvested from the array.

As shown in FIG. 12, the method 200 can additionally or alternatively include Block S260, which recites: encapsulating the set of cells at the array within an encapsulation matrix. Block S230 functions to isolate captured cells of interest at the set of wells, in order to facilitate further processing and analysis of the set of cells in at least one of single-cell format and single-cluster format. The encapsulation matrix preferably isolates a well and its contents within the array, in an embodiment of the system 100 described above; however, the encapsulation matrix can isolate particles in any other manner and/or in any other suitable system. The encapsulation matrix preferably has a flow state and a set state, wherein a photochemical reaction, thermochemical reaction, polymerization reaction and/or any other suitable reaction switches the encapsulation matrix from the flow state to the set state. In the flow state, the encapsulation matrix is preferably substantially viscous, such that the encapsulation matrix does not flow into the pores during introduction into the system 100. In the set state, the encapsulation matrix is preferably a solid or gel that prevents particle egress from the pores 111 (e.g., egress of cells, reagent particles, and large nucleic acid molecules from the pores), and is preferably porous or selectively permeable to permit small molecule, buffer, and reagent (e.g., detergent, enzyme, primer, etc.) penetration therethrough. Furthermore, by changing the constituents of a buffer or reagent and allowing sufficient time for diffusion, specific reagents/buffers can be entered into or eluted out from encapsulated cells. In one variation, the encapsulation matrix is a microporous agarose gel with a low melting point, and in another variation, the encapsulation matrix is a photopolymerizable hydrogel, such as PEG or polyacrylamide with photoinitiator; however, the encapsulation matrix can alternatively be any suitable material with any other suitable polymerization agent.

In relation to the system 100 described in Section 1 above, the encapsulation matrix can isolate contents of the set of wells between at least one of a first encapsulation layer and a second encapsulation layer, such that Block S260 includes delivering the encapsulation matrix into a fluidic network defined between the substrate, the first encapsulation layer, and/or the second encapsulation layer in a flow state prior to setting the encapsulation matrix. As such, variations of Block S260 can include delivering the encapsulation matrix to the array through an opening that provides access to the array (e.g., a fluid port), or in any other suitable manner.

Also shown in FIG. 12, the method 200 can additionally or alternatively include Block S270, which recites: diffusing a second process reagent across the encapsulation matrix S270 and through at least one of the base surface and the open surface of a well of the array. The second process reagent can include any one or more of: a lysing reagent, a fixing reagent, a permeabilization reagent, a stain, a reagent for immunochemistry, a reagent for an in-situ hybridization assay (e.g., a fluorescence in-situ hybridization assay, FISH) for nucleic acids (e.g., DNA, RNA, mRNA, etc.), a reagent for polymerase chain reaction (PCR), a culture reagent (e.g., media) for cell maintenance and/or subsequent harvesting from the array, and any other suitable reagent, as in Block S230. The second process reagent is preferably diffused across the encapsulation matrix, to contents of the set of wells through the base surfaces of the wells of the set of wells, but can additionally or alternatively be diffused across the encapsulation matrix, to contents of the set of wells through the open surfaces of the wells of the set of wells. As such, in relation to the system 100 described in Section 1 above, Block S250 can include removing at least one of the second encapsulation layer and the first encapsulation layer, and providing a reagent at the exposed surface(s) of the substrate to facilitate diffusing of the second process reagent (s) into the wells of the array. Block S250 preferably includes delivering the second process reagent(s) uniformly to each well of the set of wells of the array; however, Block S250 can alternatively include delivering the second process reagent(s) non-uniformly to the set of wells of the array. Furthermore, Block S250 can additionally or alternatively include actively driving the second process reagent(s) across the encapsulation matrix, for instance, by providing pressure (e.g., positive pressure, negative pressure) at the array or by providing centripedal force at the array.

The method 200 can additionally or alternatively include any other suitable steps or blocks that facilitate reception, processing, and/or analysis of the cell population in at least one of single-cell format and single-cluster format.

2. Method—Specific Applications

In a first specific application, the method 200 is configured to facilitate automated FISH analysis of intracellular DNA of a cell population (e.g., from a patient) at an embodiment of the system 100 described in Section 1 above. Furthermore, variations of the first specific application can include performing immunochemistry following performance of the FISH analysis, in order to characterize the cell population. The first specific application can thus facilitate recommendation of therapies target to the patient providing a biological sample including the cell population, in a patient-specific manner. In some examples, the therapies can include Herceptin for Her-2 positive patients, and Xalkori for ALK-positive non-small cell lung cancer patients.

In a second specific application, the method 200 is configured to facilitate automated FISH analysis of intracellular mRNA of a cell population (e.g., from a patient) at an embodiment of the system 100 described in Section 1 above, in order to characterize the cell population. In the second specific example, the FISH analysis includes quantitative analysis of mRNA expression for each cell, including multiplexing of multiple biomarkers (e.g., 6 biomarkers) for each cell using a set of fluorophores provided in a suitable process reagent.

In a third specific application, the method 200 is configured to facilitate FISH analysis of intracellular mRNA of a cell population (e.g., from a patient) at an embodiment of the system 100 described in Section 1 above. Furthermore, variations of the third specific application can include performing immunochemistry in combination with performance of the FISH analysis, in order to characterize the cell population. In an example, SUM159 breast cancer cells, pre-selected for CD44+ and CD24− antibodies, and isolated in at least one of single-cell format and single-cluster format can be analyzed with immunochemistry and FISH assays in the third specific application.

In a fourth specific application, the method 200 is configured to facilitate capture of viable cancer cells at an embodiment of the system 100 described in Section 1 above. In the fourth specific application, the captured cells are then harvested from the array after a period of incubation, for use in applications including drug discovery testing, sequencing of cells (e.g., CTCs), and development of improved cancer cell characterization assays.

The system 100 and method 200 of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of a processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for isolating cells in at least one of single cell format and single-cluster format, comprising:

a substrate having a broad surface;

an array comprising a set of wells defined at the broad surface of the substrate, each well of the set of wells including:
a base surface,
an open surface directly opposing the base surface, defined at the broad surface of the substrate, and sized to receive one of a single cell and a single cluster of cells from a direction perpendicular to the broad surface of the substrate, and
a first set of channels that fluidly couple each well to at least one adjacent well in the set of wells;
wherein the set of wells includes an interior subset and an exterior subset fluidly coupled to and surrounding the interior subset by way of the first set of channels; and
an encapsulation module removably coupled to the substrate at an interface, wherein the encapsulation module and the substrate cooperatively isolate each well of the set of wells to form an encapsulated array, the encapsulated array comprising the set of wells and an encapsulation layer of the encapsulation module;
a fluid delivery module surrounding the array and fluidly coupled to each well in the set of wells, the fluid delivery module comprising an inlet fluidically coupled to each of the set of wells by a second set of channels, wherein each of the second set of channels comprises an identical length; and
a perimeter channel directly fluidly coupled to the inlet and to each well of the exterior subset of the set of wells, the exterior subset of the set of wells positioned at an outermost edge of the array.

2. The system of claim 1, wherein the set of wells is arranged in a hexagonal close-packed configuration.

3. The system of claim 1, wherein at least two of the set of wells are separated by a channel of the first set of channels having a characteristic dimension less than the diameter of a single cell such that fluid flow between the two wells is unrestricted and single cell transport between the two wells is restricted.

4. The system of claim 1, further comprising a cell removal module that retains at least one of a single cell and a single cluster of cells away from the subset of the set of wells upon application of a pressure force by a pump.

5. The system of claim 4, the cell removal module comprising a cell removal tool including a tip comprising a first hollow needle and a second hollow needle, the tip configured to interface with a well of the set of wells in producing a first seal between the first hollow needle and an inlet channel of the well, and a second seal between the second hollow needle and an outlet channel of the well, the first and second hollow needle forming a unidirectional fluidic pathway in combination with the well.

6. The system of claim 1, wherein the encapsulation layer forms a boundary that isolates each well of the set of wells from each other well of the set of wells upon coupling of the encapsulation layer to the broad surface of the substrate.

7. The system of claim 6, further comprising a second encapsulation layer, wherein the second encapsulation layer is positioned between the set of wells and the substrate such that the second encapsulation layer defines the base surface of each of the set of wells, and wherein the encapsulation layer, the set of wells, and the second encapsulation layer cooperatively form an encapsulation volume.

8. The system of claim 1, wherein the encapsulation module further comprises an encapsulation matrix fluidly positioned between the encapsulation layer and the set of wells to form an encapsulation volume spanning the set of wells and the set of channels for each well in the set of wells.

9. The system of claim 8, wherein the encapsulation matrix is operable between a flow state and a set state, wherein in the flow state, the encapsulation matrix is substantially viscous and the encapsulation volume is distinct from the interior volume of the set of wells, and wherein in the set state, the encapsulation matrix is substantially rigid and the encapsulation volume occupies at least a portion of the interior volume of the set of wells.

10. The system of claim 9, wherein the encapsulation matrix is operable between the flow state and the set state by at least one of a photochemical reaction, a phase transition, a thermochemical reaction, and a polymerization reaction.

11. The system of claim 1, wherein the base surface of each of the set of wells is characterized by a surface morphology having a characteristic porosity, a characteristic concavity, and a cell retaining surface treatment.

12. The system of claim 1, wherein the array is separated from the broad surface of the substrate by a void, and wherein the set of wells are mutually fluidically coupled by the void.

13. The system of claim 1, wherein the open surface of each of the set of wells further comprises a lip with a characteristic dimension smaller than a characteristic dimension of the base surface.

14. The system of claim 1, wherein each of the set of wells includes a wall, each well separated from each other well by a corresponding wall, wherein each corresponding wall partially extends between the base surface and the open surface in defining a void between the wall of each of the set of wells and the base surface, each of the wells fluidically coupled to at least one other of the set of wells by way of the void.

15. The system of claim 1, wherein the set of wells comprises a plurality of subsets of wells, wherein the wells of each subset of the set of wells comprises a corresponding characteristic dimension, and wherein the corresponding characteristic dimension of each subset differs.

16. The system of claim 15, wherein a first subset of the set of wells is enclosed by a second subset of the set of wells, wherein the characteristic dimension of the first subset is larger than the characteristic dimension of the second subset such that the characteristic dimension decreases in a radial direction defined between a central region and an edge region of the array.

17. The system of claim 1, wherein a characteristic dimension of each well in the set of wells at least one of increases and decreases along a direction substantially aligned between the base surface and the open surface.

* * * * *